United States Patent
Harada et al.

[11] Patent Number: 6,083,955
[45] Date of Patent: Jul. 4, 2000

[54] ARYLETHENESULFONAMIDE DERIVATIVES AND DRUG COMPOSITION CONTAINING THE SAME

[75] Inventors: Hironori Harada, Matsudo; Jun-ichi Kazami, Toride; Susumu Watanuki, Tsukuba; Ryuji Tsuzuki, Tomobehiga; Katsumi Sudou, Urawa; Akihiro Tanaka, Tsuchiura, all of Japan

[73] Assignee: Yamanouchi Pharmaceutical Co., Ltd., Tokyo, Japan

[21] Appl. No.: 09/091,524

[22] PCT Filed: Dec. 19, 1996

[86] PCT No.: PCT/JP96/03701

§ 371 Date: Jun. 19, 1998

§ 102(e) Date: Jun. 19, 1998

[87] PCT Pub. No.: WO97/22595

PCT Pub. Date: Jun. 26, 1997

[30] Foreign Application Priority Data

Dec. 20, 1995 [JP] Japan ................................ 7-332111

[51] Int. Cl.[7] ............... A61K 31/505; C07D 239/48; C07D 239/54
[52] U.S. Cl. ............ 514/269; 544/296; 544/298; 544/319; 544/327
[58] Field of Search .................... 544/296, 319, 544/327, 269, 298; 514/269

[56] References Cited

FOREIGN PATENT DOCUMENTS

| | | |
|---|---|---|
| 0510526A1 | 4/1992 | European Pat. Off. . |
| 0526708A1 | 6/1992 | European Pat. Off. . |
| 0601386A1 | 11/1993 | European Pat. Off. . |
| 0633259A1 | 6/1994 | European Pat. Off. . |
| 0 658 548 A1 | 6/1995 | European Pat. Off. . |
| 7-332111 | 12/1920 | Japan . |
| WO 94/27979 | 12/1994 | WIPO . |

OTHER PUBLICATIONS

Sakuma et al. JP 07061985, Caplus Abstract 1–2, 1995.
Douglas S. A. Clinical development of endothelin receptor antagonists. TIPS –Nov. 1997, 408–412.

*Primary Examiner*—Richard L. Raymond
*Assistant Examiner*—V Balasubramian
*Attorney, Agent, or Firm*—Finnegan, Henderson, Farabow, Garrett & Dunner, L.L.P.

[57] ABSTRACT

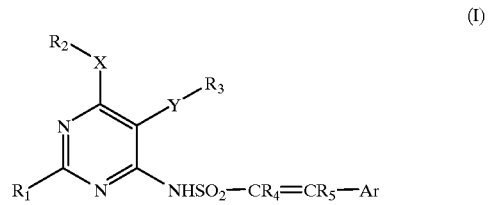

Novel arylethenesulfonamide derivative having a high affinity for drugs, especially endoserine receptors, and represented by general formula (I); pharmaceutically acceptable salts thereof; and drugs comprising the same as the active ingredient, especially endoserine receptor antagonist, wherein Ar: optionally substituted aryl group or optionally substituted five- to six-membered heteroaryl group;

X: oxygen atom, sulfur atom or a group represented by a formula —NH—;

Y: oxygen atom or sulfur atom;

$R_1$: hydrogen atom, optionally halogen-substituted lower alkyl group, cycloalkyl group, optionally substituted aryl group or optionally substituted five- to six-membered heteroaryl group.

$R_2$: lower alkyl group, lower alkenyl group or lower alkynyl group where each of which may be substituted with one to three substituent(s) selected from a group consisting of hydroxyl group, lower alkoxy group, cycloalkyl group, halogen atom, carboxyl group and lower alkoxycarbonyl group;

$R_3$: phenyl group which may be substituted with one to four substituent(s) selected from a group consisting of optionally halogen-substituted lower alkyl group, lower alkoxy group, halogen atom, lower alkylthio group, lower alkylsulfinyl group, lower alkanesulfonyl group, carboxyl group, lower alkoxycarbonyl group and carbamoyl group; and $R_4$ and $R_5$: they may be same or different and each is hydrogen atom or lower alkyl.

8 Claims, No Drawings

ARYLETHENESULFONAMIDE DERIVATIVES AND DRUG COMPOSITION CONTAINING THE SAME

This application is a 371 of PCT/JP96/03701, filed Dec. 19, 1996.

TECHNICAL FIELD

The present invention relates to pharmaceuticals, more particularly, novel arylethenesulfonamide derivatives having a high affinity to endothelin receptor, pharmaceutically-acceptable salts thereof and pharmaceutical compositions containing the same, particuarly an antagonist to endothelin receptor.

BACKGROUND ART

Endothelin is an endogenous physiologically active peptide consisting of 21 amino acids and it has been known that, in endothelin, there are three isopeptides of ET-1, ET-2 and ET-3 wherein the amino acid sequences are somewhat different.

Endothelin expresses its physiological action by binding to an endothelin receptor on a target cell membrane. For endothelin receptor, it has been clarified until now that there are at least two subtypes and those subtypes are named $ET_A$ and $ET_B$, respectively. Those receptors differ in their affinity to endothelin. $ET_A$ receptor has a higher affinity to ET-1 and Et-2 than to ET-3 while $ET_B$ receptor has the affinity of a similar degree to the three types of endothelin.

Endothelin and endothelin receptor are produced and expressed, respectively, in various cells of various organs and varieties of physiological actions which are caused by them have been known. For example, in blood vessel, ET-1 which is produced and secreted in vascular endothelial cells bound $ET_A$ receptor on smooth muscle cells of blood vessel existing near there and contracts the blood vessel strongly and continuously. On the other hand, vascular endothelial cells themselves express $ET_B$ receptor and, when ET-1 is bonded thereto, nitrogen monoxide (NO) is produced and released. Nitrogen monoxide has an action of relaxing the smooth muscle of blood vessel. In fact, when ET-1 is intravenously injected to rat experimentally, long-lasting hypertension is observed after a transient hypotension.

As noted from the physiological action in blood vessel as mentioned above, ET-1 has an aspect as a physiologically active peptide having a very strong and continuous contraction to blood vessel and, because of that, its relation to diseases, particularly to cardiovascular diseases, has been discussed since the time when it was found.

Today, it is pointed out that there is a possibility that an excessive secretion of endothelin, particularly ET-1 (to be more specific, an increase in ET-1 concentration either topically or in tissues and circulating blood), participates not only in cardiovascular diseases but also in many other diseases. Thus, it was reported to participate, for example, in essential hypertension, pulmonary hypertension, hypertension induced by erythropoietin, hypertension induced by cyclosporin A, bronchial asthma, acute renal failure, chronic renal failure, glomerular nephritis, renal failure induced by cyclosporin, acute myocardial infarction, unstable angina, congestive heart failure, cerebrovascular spasm mostly after subarachnoid hemorrhage, cerebroischemic disturbance, urinary incontinence, benign prostatic hypertrophy, arteriosclerosis, Raynaud's syndrome, diabetic peripheral circulatory disturbance, diabetic renal diseases, preeclampsia, premature delivery, digestive ulcer, hepatic failure, rheumatism, restenosis after PTCA, chronic respiratory failure, chronic obstructive pulmonary diseases, cor pulmonale, acute respiratory failure, pulmonary edema, ischemic hepatic disturbance, adult respiratory distress syndrome, interstitial pneumonia, pulmonary fibrosis, glaucoma, osteoarthritis, chronic articular rheumatism, hepatic cirrhosis, inflammatory bowel diseases (IBD), cancer, etc. (G. M. Rubanyi, M. A. Plokoff, Pharmacological Reviews, vol. 46, no. 3, 325 (1994); Saishin Igaku, vol. 49, no.3, 335 (1994); Kidney International, 37, 1487–1491 (1990); Lancet, 339, 381–385(1992); Cell Mol. Neurobiol., 13, 15–23 (1993); J. Clin. Encocrino. Metab., 76, 378–383 (1993); J. Clin. Pathol., 48(6), 519–524 (1995); Chest, 104(2), 476–480(1993); Am. J. Med., 99(3), 155–160 (1995); Hepatology, 16, 95–99 (1992); etc.).

Accordingly, pharmaceuticals which inhibit the binding of ET-1 to endothelin receptor by bonding to endothelin receptor, i.e. endothelin receptor antagonists, can be effective preventive and therapeutic agents to the diseases as mentioned hereinabove.

With regard to such endothelin receptor antagonists, a series of benzenesulfonamide derivatives is disclosed in the Japanese Laid-Open Patent Publications Hei-05/155,864, Hei-05/222,003, Hei-06/211,810 and Hei-07/017,972. In particular, a compound which is represented by the following formula

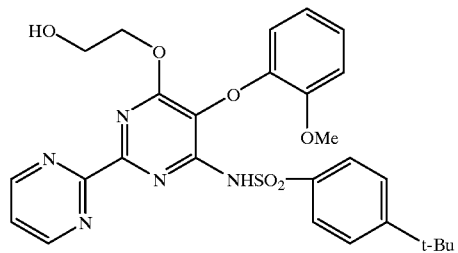

which is disclosed in Example 67 of the Japanese Laid-Open Patent Publication Hei-05/222,003 (generic name: Bosentan) has been reported for its effectiveness and absorption by oral administration in pathogenic animal models (J. Pharmacol. Exp. Ther., 270(1), 228–2345, 1994; Hypertension, 224, 183–188, 1994; Clin. Pharmacol. Ther., 60, 124–137, 1996).

DISCLOSURE OF THE INVENTION

An object of the present invention is to offer novel compounds having far better antagonizing action to endothelin receptor.

The present inventors have proceeded a screening for the compounds having a high affinity to endothelin receptor and, as a result, they have found that novel arylethenesulfonamide derivatives which are different from conventional compounds in such a respect that arylethene group is substituted at sulfonamide of a pyrimidine ring exhibit a high affinity to endothelin receptor, particularly to $ET_A$ receptor, and strongly antagonize whereupon the present invention has been achieved.

Thus, the present invention relates to a novel arylethenesulfonamide derivative represented by the following formula (I) or a pharmaceutically acceptable salt thereof.

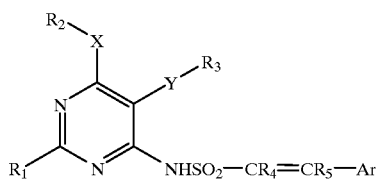

(In the formula,
Ar: optionally substituted aryl group or optionally substituted five- to six-membered heteroaryl group;
X: oxygen atom, sulfur atom or a group represented by a formula —NH—;
Y: oxygen atom or sulfur atom;
$R_1$: hydrogen atom, optionally halogen-substituted lower alkyl group, cycloalkyl group, optionally substituted aryl group or optionally substituted five- to six-membered heteroaryl group;
$R_2$: lower alkyl group, lower alkenyl group or lower alkynyl group where each of which may be substituted with one to three substituent(s) selected from a group consisting of hydroxyl group, lower alkoxy group, cycloalkyl group, halogen atom, carboxyl group and lower alkoxycarbonyl group;
$R_3$: phenyl group which may be substituted with one to four substituent(s) selected from a group consisting of optionally halogen-substituted lower alkyl group, lower alkoxy group, halogen atom, lower alkylthio group, lower alkylsulfinyl group, lower alkanesulfonyl group, carboxyl group, lower alkoxycarbonyl group and carbamoyl group; and
$R_4$ and $R_5$: they may be same or different and each is hydrogen atom or lower alkyl group)

Preferred compounds which are preferred in the present invention are arylethenesulfonamide derivatives represented by the above-mentioned formula (I) in which:

Ar is an aryl group which may be substituted with one to five substituent(s) selected from a group consisting of lower alkyl group (said lower alkyl group may be substituted with one to four substituent(s) selected from a group consisting of halogen atom, lower alkoxy group, carboxyl group, amino group and mono- or di-lower alkylamino group), lower alkoxy group, lower alkoxycarbonyl group, carboxyl group, halogen atom, nitro group, cyano group, amino group, mono- or di-lower alkylamino group, hydroxyl group and $C_{1-3}$ alkylenedioxy group; or five- to six-membered heteroaryl group which may be substituted with one to four substituent (s) selected from a group consisting of lower alkyl group (said lower alkyl group may be substituted with one to four substituent(s) selected from a group consisting of halogen atom, lower alkoxy group, carboxyl group, amino group and mono- or di-lower alkylamino group), lower alkoxy group, lower alkoxycarbonyl group, carboxyl group, halogen atom, nitro group, cyano group, amino group, and mono- or di-lower alkylamino group; and $R_1$ is hydrogen; lower alkyl group which may be substituted with halogen atom(s); cycloalkyl group; aryl group which may be substituted with one to five substituent(s) selected from a group consisting of lower alkyl group (said lower alkyl group may be substituted with one to four substituent (s) selected from a group consisting of halogen atom, lower alkoxy group, carboxyl group, amino group and mono- or di-lower alkylamino group), lower alkoxy group, lower alkoxy-carbonyl group, carboxyl group, halogen atom, nitro group, cyano group, amino group, mono- or di-lower alkylamino group, hydroxyl group and $C_{1-3}$ alkylenedioxy group; or five- to six-membered heteroaryl group which may be substituted with one to four substituent (s) selected from a group consisting of lower alkyl group (said lower alkyl group may be substituted with one to four substituent (s) selected from a group consisting of halogen atom, lower alkoxy group, carboxyl group, amino group and mono- or di-lower alkylamino group), lower alkoxy group, lower alkoxycarbonyl group, carboxyl group, halogen atom, nitro group, cyano group, amino group, and mono- or di-lower alkylamino group;
or pharmaceutically aceptable salts thereof.

More preferred compounds are:
(1) arylethenesulfonamide derivatives represented by the above-mentioned formula (I) or salts thereof in which
Ar is aryl group which may be substituted with one to five substituent(s) selected from a group consisting of optionally halogen-substituted lower alkyl group, lower alkoxy group, lower alkoxycarbonyl group, carboxyl group, halogen atom, nitro group and cyano group; or five- to six-membered heteroaryl group which may be substituted with one to four substituent(s) selected from a group consisting of lower alkyl group and lower alkoxy group;
X is oxygen atom or a group represented by a formula —NH—;
Y is oxygen atom;
$R_1$ is optionally halogen-substituted lower alkyl group; cycloalkyl group; aryl group which may be substituted with one to five substituent(s) selected from a group consisting of optionally halogen-substituted lower alkyl group, lower alkoxy group, lower alkoxycarbonyl group, carboxyl group, halogen atom, nitro group, cyano group and $C_{1-3}$ alkylenedioxy group; or five- to six-membered heteroaryl group which may be substituted with one to four substituent(s) selected from a group consisting of optionally halogen-substituted lower alkyl group, lower alkoxy group, lower alkoxycarbonyl group, carboxyl group, halogen atom, nitro group and cyano group; and
$R_3$ is phenyl group which may be substituted with one to four substituent(s) selected from a group consisting of optionally halogen-substituted lower alkyl group, lower alkoxy group, halogen atom, carboxyl group and lower alkoxycarbonyl group;
(2) arylethenesulfonamide derivatives represented by the formula (I) or pharmaceutically acceptable salts thereof in which
Ar is five- to six-membered heteroaryl group, naphthyl group or phenyl group which may be substituted with one to five substituent(s) selected from a group consisting of optionally halogen-substituted lower alkyl group, lower alkoxy group and halogen atom;
$R_1$ is optionally halogen-substituted lower alkyl group; cycloalkyl group; phenyl group which may be substituted with one to five substituent(s) selected from a group consisting of optionally halogen-substituted lower alkyl group, lower alkoxy group, nitro group and $C_{1-3}$ alkylenedioxy group; or five- to six-membered heteroaryl group which may be substituted with one to four substituent(s) selected from a group consisting of optionally halogen-substituted lower alkyl group and lower alkoxy group;

R$_2$ is lower alkynyl group or lower alkyl group which may be substituted with one to three substituent(s) selected from a group consisting of hydroxyl group, lower alkoxy group, cycloalkyl group and halogen atom; and R$_3$ is phenyl group which may be substituted with one to four substituent(s) selected from a group consisting of lower alkyl group, lower alkoxy group and lower alkoxycarbonyl group;

(3) arylethenesulfonamide derivatives represented by the formula (I) or pharmaceutically acceptable salts thereof in which Ar is optionally lower-alkyl-substituted phenyl group or thienyl group;

X is oxygen atom;

R$_1$ is phenyl group which may be substituted with lower alkoxy group or five- to six-membered heteroaryl group which may be substituted with lower alkyl group;

R$_2$ is lower alkynyl group or lower alkyl group which may be substituted with one to three substituent(s) selected from a group consisting of hydroxyl group and halogen atom; and R$_3$ is phenyl group which is substituted with lower alkoxy group(s);

(4) arylethenesulfonamide derivatives represented by the formula (I) or pharmaceutically acceptable salts thereof in which Ar is phenyl group or thienyl group;

R$_1$ is pyrimidinyl group;

R$_2$ is lower alkyl group which may be substituted with halogen atom(s);

R$_3$ is phenyl group which is substituted with lower alkoxy group(s);

R$_4$ is hydrogen atom or lower alkyl group; and

R$_5$ is hydrogen atom; or (5) arylethenesulfonamide derivatives represented by the formula (I) or pharmaceutically acceptable salts thereof selected from a group consisting of the following compounds as well as salts thereof:

N-[6-(2-hydroxyethoxy)-5-(2-methoxyphenoxy)-2-(2-pyrimidinyl)-4-pyrimidinyl]-2-phenylethenesulfonamide, N-[6-methoxy-5-(2-methoxyphenoxy)-2-(2-pyrimidinyl)-4-pyrimidinyl]-2-phenylethenesulfonamide, N-[6-(2-fluoroethoxy)-5-(2-methoxyphenoxy)-2-(2-pyrimidinyl)-4-pyrimidinyl]-2-phenylethenesulfonamide, N-[6-(2-propynyloxy)-5-(2-methoxyphenoxy)-2-(2-pyrimidinyl)-4-pyrimidinyl]-2-phenylethenesulfonamide, N-[6-methoxy-5-(2-methoxyphenoxy)-2-(2-pyrimidinyl)-4-pyrimidinyl]-1-methyl-2-phenylethenesulfonamide, N-[6-methoxy-5-(2-methoxyphenoxy)-2-(2-pyrimidinyl)-4-pyrimidinyl]-1-ethyl-2-phenylethenesulfonamide, and N-[6-methoxy-5-(2-methoxyphenoxy)-2-(2-pyrimidinyl)-4-pyrimidinyl]-2-(2-thienyl)ethenesulfonamide.

Further, the present invention relates to a pharmaceutical composition which contains the arylethenesulfonamide derivative or pharmaceutically acceptable salt thereof and a pharmaceutically acceptable carrier and, particularly, it relates to endothelin receptor antagonists. More particularly, it relates to preventive or therapeutic agents for diseases in which endothelin receptor is participated such as essential hypertension, pulmonary hypertension, hypertension induced by erythropoietin, hypertension induced by cyclosporin A, bronchial asthma, acute renal failure, chronic renal failure, glomerular nephritis, renal failure induced by cyclosporin, acute myocardial infarction, unstable angina, congestive heart failure, cerebrovascular spasm mostly after subarachnoid hemorrhage, cerebroischemic disturbance, urinary incontinence, benign prostatic hypertrophy, arteriosclerosis, Raynaud's syndrome, diabetic peripheral circulatory disturbance, diabetic renal diseases, preeclampsia, premature delivery, digestive ulcer, hepatic failure, rheumatism, restenosis after PTCA, chronic respiratory failure, chronic obstructive pulmonary diseases, cor pulmonale, acute respiratory failure, pulmonary edema, ischemic hepatic disturbance, adult respiratory distress syndrome, interstitial pneumonia, pulmonary fibrosis, glaucoma, osteoarthritis, chronic articular rheumatism, hepatic cirrhosis, inflammatory bowel diseases (IBD), cancer, etc.

The compound (I) of the present invention will be illustrated in detail as follows.

The term "lower" used in the definitions for the groups in the formula (I) of the present specification means a straight or branched carbon chain having from one to six carbon(s) unless otherwise mentioned.

Accordingly, examples of "lower alkyl group" are methyl group, ethyl group, propyl group, isopropyl group, butyl group, isobutyl group, sec-butyl group, tert-butyl group, pentyl group, isopentyl group, neopentyl group, tert-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group and 1-ethyl-2-methylpropyl group. Among them, those having from one to four carbon(s) are preferred and methyl group, ethyl group, propyl group and isopropyl group are particularly preferred.

"Lower alkenyl group" is a straight or branched alkenyl group having from two to six carbons and its specific examples are vinyl group, allyl group, 1-propenyl group, 1-methylvinyl group, 1-butenyl group, 2-butenyl group, 3-butenyl group, 2-methyl-1-propenyl group, 2-methylallyl group, 1-methyl-1-propenyl group, 1-pentenyl group, 2-pentenyl group, 3-pentenyl group, 4-pentenyl group, 3-methyl-1-butenyl group, 3-methyl-2-butenyl group, 3-methyl-3-butenyl group, 2-methyl-1-butenyl group, 2-methyl-2-butenyl group, 2-methyl-3-butenyl group, 1-methyl-1-butenyl group, 1-methyl-2-butenyl group, 1-methyl-3-butenyl group, 1,1-dimethylallyl group, 1,2-dimethyl-1-propenyl group, 1,2-dimethyl-2-propenyl group, 1-ethyl-1-propenyl group, 1-ethyl-2-propenyl group, 1-hexenyl group, 2-hexenyl group, 3-hexenyl group, 4-hexenyl group, 5-hexenyl group, 1,1-dimethyl-1-butenyl group, 1,1-dimethyl-2-butenyl group, 1,1-dimethyl-3-butenyl group, 3,3-dimethyl-1-butenyl group, 1-methyl-1-pentenyl group, 1-methyl-2-pentenyl group, 1-methyl-3-pentenyl group, 1-methyl-4-pentenyl group, 4-methyl-1-pentenyl group, 4-methyl-2-pentenyl group and 4-methyl-3-pentenyl group and, among them, alkenyl group having from three to four carbons is preferred.

"Lower alkynyl group" is a straight or branched alkynyl group having from two to six carbons and its examples are ethynyl group, 1-propynyl group, 2-propynyl group, 1-butynyl group, 2-butynyl group, 3-butynyl group, 1-methyl-2-propynyl group, 1-pentynyl group, 2-pentynyl group, 3-pentynyl group, 4-pentynyl group, 3-methyl-1-butynyl group, 2-methyl-3-butynyl group, 1- methyl-2-butynyl group, 1-methyl-3- butynyl group, 1,1-dimethyl-2-propynyl group, 1-hexynyl group, 2-hexynyl group, 3-hexynyl group, 4-hexynyl group and 5-hexynyl group. Among them, the alkynyl group having from three to four carbons is preferred.

"Aryl group" in the "optionally substituted aryl group" stands for an aromatic hydrocarbon group. Preferably, it is an aryl group having from 6 to 14 carbons and its examples are phenyl group, naphthyl group, indenyl group, anthryl group and phenanthryl group. More preferably, it is phenyl group and naphthyl group.

Those groups may be substituted with one or more substituent(s) or, preferably, with one to five substituent(s). Any substituent may be used therefor so far as it is a substituent which is commonly used as a substituent for aryl group. Preferred examples are lower alkyl group (said lower alkyl may be substituted with from one to four substituent(s) selected from a group consisting of halogen atom, lower alkoxy group, carboxyl group, amino group and mono- or di-lower alkylamino group), lower alkoxy group, lower alkoxycarbonyl group, carboxyl group, halogen atom, nitro group, cyano group, amino group, mono- or di-lower alklamino group, hydroxyl group and $C_{1-3}$ alkylenedioxy group.

The term "five- to six-membered heteroaryl group" in "optionally substituted five- to six-membered heteroaryl group" stands for five- to six-membered monocyclic heteroaryl group containing from one to four hetero atom(s) selected from nitrogen atom, sulfur atom and oxygen atom and its specific examples are furyl group, thienyl group, pyrrolyl group, imidazolyl group, pyrazolyl group, thiazolyl group, isothiazolyl group, oxazolyl group, isoxazolyl group, triazolyl group, oxadiazolyl group, thiadiazolyl group, tetrazolyl group, pyridyl group, pyrimidinyl group, pyridazinyl group and pyrazinyl group.

Preferred examples of "optionally substituted five- to six-membered heteroaryl group" for Ar in the present invention are furyl group, thienyl group, pyrrolyl group, imidazolyl group, thiazolyl group, isothiazolyl group, oxazolyl group and isoxazolyl group and particularly preferred examples are furyl group and thienyl group. Examples of the preferred groups for $R_1$ are furyl group, thienyl group, thiazolyl group, pyridyl group and pyrimidinyl group and, pariticularly preferably, pyrimidinyl group.

Those groups may be substituted with one or more any substituent(s) or, preferably, from one to four substituent(s). Any substituent may be used so far as it is a substituent which is commonly used as a substituent for heteroaryl group. Preferred examples are lower alkyl group (said lower alkyl group may be substituted with from one to four substituent (s) selected from a group consisting of halogen atom, lower alkoxy group, carboxyl group, amino group and mono- or di-lower alkyl-amino group), lower alkoxy group, lower alkoxycarbonyl group, carboxyl group, halogen atom, nitro group, cyano group, amino group or mono- or di-lower alkyl-amino group.

Preferred "cycloalkyl group" is a cycloalkyl group having from three to eight carbons. Its specific examples are cyclopropyl group, cyclobutyl group, cyclopentyl group, cyclohexyl group, cycloheptyl group and cyclooctyl group and preferred examples are cyclopropyl group, cyclobutyl group, cyclopentyl group and cyclohexyl group.

Examples of "lower alkoxy group" are methoxy group, ethoxy group, propoxy group, isopropoxy group, butoxy group, isobutoxy group, sec-butoxy group, tert-butoxy group, pentyloxy group (amyloxy group), isopentyloxy group, tert-pentyloxy group, neopentyloxy group, 2-methylbutoxy group, 1,2-dimethylpropoxy group, 1-ethylpropoxy group and hexyloxy group. Among them, those having from one to four carbons are preferred and methoxy group and ethoxy group are particularly preferred.

Examples of "halogen atom" are fluorine atom, chlorine atom, bromine atom and iodine atom and preferred examples are fluorine atom and chlorine atom.

Lower alkyl group which is substituted with halogen atom(s) in "optionally halogen-substituted lower alkyl group" is a group in which one or more hydrogen atom(s) is/are substituted with the above-mentioned halogen atom (s). Preferably, it is lower alkyl group substituted with one to four halogen atom(s) such as chloromethyl group, fluoromethyl group, bromomethyl group, iodomethyl group, dichloromethyl group, difluoromethyl group, dibromomethyl group, trichloromethyl group, trifluoromethyl group, 2-chloroethyl group, 2-fluoroethyl group, 2-bromoethyl group, 2-iodoethyl group, 2,2-dichloroethyl group, 2,2-difluoroethyl group, 2,2-dibromoethyl group, 2,2,2-trichloroethyl group, 2,2,2 -trifluoroethyl group, 1-chloroethyl group, 1-fluoroethyl group, 1-bromoethyl group, 1-iodoethyl group, 1,2-dichloroethyl group, 1,2-difluoroethyl group, 1,1-dibromoethyl group, 1,2,2-trichloroethyl group, 1,2,2-trifluoroethyl group, 1-bromo-2-chloroethyl group, 3-chloropropyl group, 3-fluoropropyl group, 3,3-dichloropropyl group, 3,3-difluoropropyl group, 3,3,3-trifluoropropyl group, 4-chlorobutyl group and 5-fluoropentyl group. Among them, lower alkyl group having from 1 to 3 carbon(s) substituted with from 1 to 3 chlorine or fluorine atom(s) is preferred and particularly preferred one is trifluoroemethyl group.

"Lower alkoxycarbonyl group" is a group in which an ester is formed from carboxyl group and a straight or branched alcohol having from one to six carbon(s) and its examples are methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, tert-pentyloxycarbonyl group and hexyloxycarbonyl group. Among them, those having from one to four carbon(s) are preferred and methoxycarbonyl group and ethoxycarbonyl group are particularly preferred.

"Lower alkylthio group" is a group in which hydrogen atom of the mercapto group is substituted with the above-mentioned "lower alkyl group" and its specific examples are methylthio group, ethylthio group, propylthio group, isopropylthio group, butylthio group, isobutylthio group, pentylthio group, isopentylthio group and hexylthio group. Among them, alkylthio group having from one to four carbon(s) are preferred and those having from one to three carbon(s) such as methylthio group, ethylthio group, propylthio group and isopropylthio group are particularly preferred.

Examples of "lower alkylsulfinyl group" are methylsulfinyl group, ethylsulfinyl group, propylsulfinyl group, isopropylsulfinyl group, butulsulfinyl group, isobutylsulfinyl group, pentylsulfinyl group, isopentylsulfinyl group, hexylsulfinyl group and isohexylsulfinyl group. Among them, alkylsulfinyl group having from one to four carbon(s) are preferred and those having from one to three carbon(s) such as methylsulfinyl group, ethylsulfinyl group, propylsulfinyl group and isoproplsulfinyl group are particularly preferred.

Examples of "lower alkanesulfonyl group" are methanesulfonyl group, ethanesulfonyl group, propanesulfonyl group, isopropanesulfonyl group, butanesulfonyl group, isobutanesulfonyl group, pentanesulfonyl group, isopentanesulfonyl group, hexanesulfonyl group and isohexanesulfonyl group. Among them, alkylsulfonyl groups having from one to four carbon(s) are preferred and those having from one to three carbon(s) such as methanesulfonyl group, ethanesulfonyl group, propanesulfonyl group and isopropanesulfonyl group are particularly preferred.

"Mono- or di-lower alkyl-amino group" is an amino group in which one or two hydrogen atom(s) is/are substituted with the above-mentioned alkyl group(s). In the case of di-lower alkyl-amino group, the two alkyl groups may be either same or different. Examples of the mono-(lower alkyl)-amino group are methylamino group, ethylamino group, propylamino group, isopropylamino group, butylamino group, isobutylamino group, sec-butylamino group, tert-butylamino group and pentylamino group while examples of di-(lower alkyl)-amino group are dimethylamino group, diethylamino group, dipropylamino group, methylethylamino group, methylpropylamino group, methylisopropylamino group, methylbutylamino group, methylisobutylamino group, ethylpropylamino group and ethylisopropylamino group.

Specific examples of "$C_{1-3}$ alkylenedioxy group" are methylenedioxy group, ethylenedioxy group and propylenedioxy group.

In the compounds of the present invention, there are geometrical isomers such as cis- and trans-compounds [or (E) compound and (Z) compound] due to double bonds and the present invention covers each of the separated isomer [(E) compound or (Z) compound] and a mixture thereof. In the present invention, the compound in which the groups $R_4$ and $R_5$ are in a transconfiguration is particularly preferred.

Besides the above, geometrical isomers and tautomers may be present depending upon the types of the substituents and the present invention covers each of the separated isomers and a mixture thereof.

In addition, compounds of the present invention may have asymmetric carbon atoms and optical isomers [(R) compound and (S) compound] due to that may be present. The present invention covers a mixture of those optical isomers and also a compound separated therefrom.

The compound (I) of the present invention may form an acid addition salt or, depending upon the type of the substituent(s), salt with a base may be formed as well. Such a salt is a pharmaceutically acceptable salt and its specific examples are acid addition salt such as a salt with inorganic acid (for example, hydrochloric acid, hydrobromic acid, hydroiodic acid, sulfuric acid, nitric acid and phosphoric acid) or organic acid (for example, formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid) and a salt with base such as inorganic base (for example, sodium, potassium, magnesium, calcium and aluminum) and organic base (for example, methylamine, ethylamine, ethanolamine, lysine and ornithine) as well as ammonium salt.

The present invention further covers various kinds of hydrates and solvates of the compounds (I) of the present invention and salts thereof as well as polymorphic crystals.
(Manufacturing Methods)

Compounds of the present invention and pharmaceutically acceptable salts thereof may be manufactured by application of various known synthetic methods utilizing the characteristics based upon the type of their fundamental skeleton or substituents. At that time, it is sometimes effective in the manufacturing technique that, depending upon the type of the functional group, said functional group is substituted with an appropriate protective group, that is a group which can be easily converted to said functional group. After that, the protective group is removed if necessary whereupon a desired compound is afforded. Examples of such a functional group are hydroxyl group and carboxyl group while examples of the protective group therefor are those which are mentioned, for example, in "Protective Groups in Organic Synthesis" (second edition) by Greene and Wuts and they may be appropriately used depending upon the reaction conditions.

Representative manufacturing methods of the compounds of the present invention will be given as hereunder.

First Manufacturing Method.

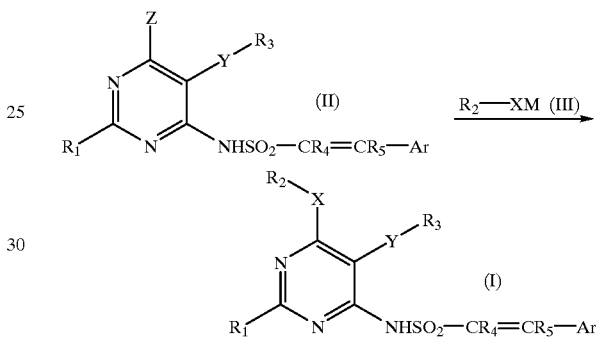

(In the formulae, Z is a leaving group such as halogen atom and organic sulfonic acid residue; and M is hydrogen atom or alkali metal atom)

Examples of the sulfonic acid residue are alkanesulfonyloxy group such as methanesulfonyloxy group and ethanesulfonyloxy group and aromatic sulfonyloxy group such as benzenesulfonyloxy group and toluenesulfonyloxy group (particularly, p-toluenesulfonyloxy group).

Examples of the alkali metal atom are sodium and potassium.

Compound of the present invention (I) is obtained by the reaction of a compound represented by the formula (II) having an appropriate leaving group with alcohol, thiol, amine or alkali metal substituent represented by the formula (III) to conduct etherization or N-alkylation.

It is advantageous to conduct this reaction in such a manner that the compound (II) is made to react with the compound (III) in an amount corresponding to the reaction in the presence or absence of an inert solvent such as benzene, xylene, tetrahydrofuran (THF), ether, dioxane, dimethylformamide (DMF), dimethyl sulfoxide, methylene chloride, dichloromethane, dichloroethane and chloroform in the presence of, if necessary, inorganic base such as sodium, sodium hydride, sodium hydroxide, potassium hydroxide and potassium carbonate or organic base such as trimethylamine, triethylamine, pyridine, picoline, lutidine and N,N-dimethylaniline with cooling, at room temperature or with warming depending upon the reaction.

Second Manufacturing Method

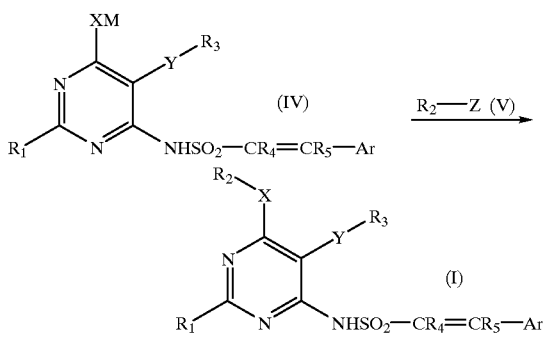

Compound of the present invention (I) can be manufactured by the reaction of a compound of a formula (IV) having hydroxyl group, mercapto group or alkali metal substitute thereof with a compound of a formula (V) having an appropriate leaving group.

The compound can be conducted by the same manner as in the First Manufacturing Method.

Third Manufacturing Method

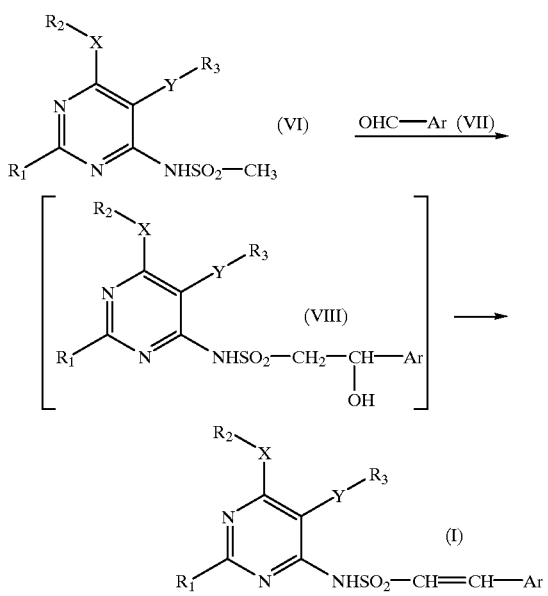

Compound of the present invention (I) can be manufactured as follows. Thus, a methanesulfonic acid derivative of a formula (VI) is made to react with a benzaldehyde derivative of a formula (VII) (the first step) and the resulting alcohol compound of a formula (VIII) is subjected to a dehydrating reaction (the second step).

It is advantageous to conduct the first step in such a manner that a methanesulfonic acid derivative (VI) is made to react with a benzaldehyde derivative (VII) in a corresponding amount to the reaction in an inert solvent such as diethyl ether, THF, DMF and benzene in the presence of a base such as sodium hydride, potassium carbonate, sodium carbonate, n-butyl lithium and N,N,N',N'-tetramethylethylenediamine at the temperature range of from −60° C. to warm temperature.

It is advantageous to conduct the second step in such a manner that the alcohol compound (VIII) is kept at room temperature to with warming in an inert solvent such as benzene and methylene chloride.

If desired, a dehydrating agent such as pyrimidinium p-toulenesulfonate, sulfuric acid and mesyl chloride-triethylamine may be added thereto.

As hereunder, representative methods for the manufacture of starting materials will be mentioned in detail.

Manufacturing Method A

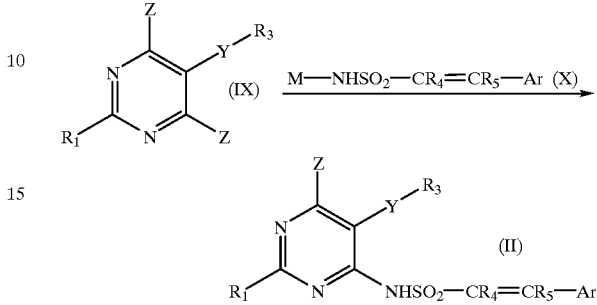

The starting compound (II) in the First Manufacturing Method can be prepared by the reaction of pyrimidine dihalide (IX) with arylethenesulfonamide (X) or a salt thereof. The pyrimidine dihalide (IX) can be manufactured by a method mentioned in the Japanese Laid-Open Patent Publication Hei-05/222,003 or a method similar thereto. Salt (X) of the arylethenesulfonamide can be manufactured by the reaction of a free sulfonamide with an appropriate inorganic base.

Manufacturing Method B

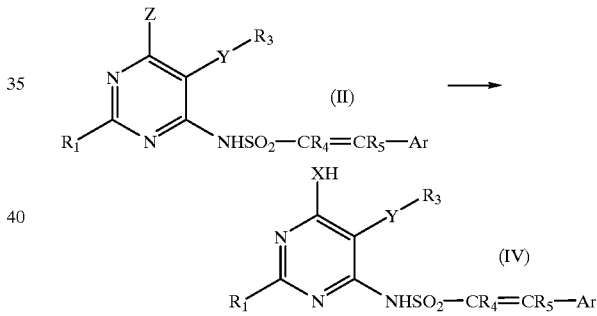

The compound (IV) which is a starting material for the Second Manufacturing Method is prepared by the reaction of a halide of a formula (II) with a sulfurizing agent such as sodium hydrosulfide, hydroxide such as sodium hydroxide or aminating agent such as ammonia.

The compound in which X is a sulfur atom in the above formulae is prepared by a sulfurizing reaction.

It is advantageous to conduct the reaction in such a manner that the halide (II) is made to react with a sulfurizing agent such as hydrogen sulfide and sodium hydrosulfide in an amount corresponding to the reaction in an inert solvent such as toluene, benzene, chloroform, THF and DMF at room temperature to with warming.

Manufacturing Method C

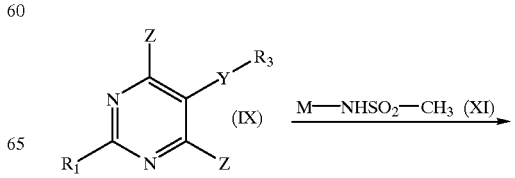

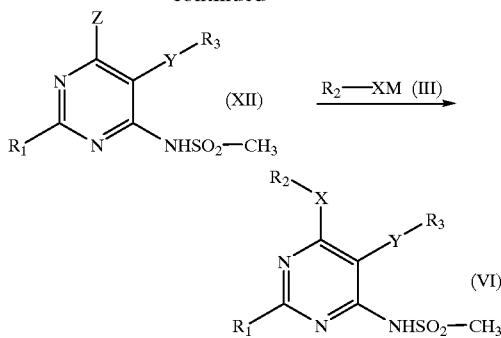

The starting material (VI) in the Third Manufacturing Method is prepared as follows. Thus, the compound (IX) is made to react with a methanesulfonamide derivative (XI) (the first step) and the resulting compound (XII) is made to react with a compound (III) (the second step).

With regard to the first step, it is advantageous to conduct the reaction under the same conditions as in the Manufacturing Method A.

With regard to the second step, it is advantageous to conduct the reaction under the same conditions as in the First Manufacturing Method.

The reaction product obtained by each of the above-mentioned manufacturing methods is liberated and purified as a free compound or salt or solvate thereof such as a hydrate. Salt can be manufactured by means of a common salt-forming reaction.

Isolation and purification can be conducted by means of common chemical operations such as extraction, concentration, evaporation, crystallization, filtration, recrystallization and various chromatographic techniques.

Each of the isomers can be separated by common means utilizing the physico-chemical differences between the isomers. In the case of optical isomers for example, they can be separated by common racemic resolution means such as fractional crystallization and chromatography. With regard to an optical isomer, it is also possible to synthesize said isomer from an appropriate optically active starting compound.

(Industrial Applicability)

The compounds of the present invention have an affinity to endothelin receptors and they especially have a high affinity to an $ET_A$ receptor which is one of subtypes of the endothelin receptors.

Accordingly, the compounds of the present invention exhibit an action of competitively inhibiting the binding of endothelin to receptors and can be used for the treatment of various diseases in which endothelin is participated such as cardiovascular diseases. Examples of such diseases are essential hypertension, pulmonary hypertension, hypertension induced by erythropoietin, hypertension induced by cyclosporin A, bronchial asthma, acute renal failure, chronic renal failure, glomerular nephritis, renal insufficiency induced by cyclosporin, acute myocardial infarction, unstable angina, congestive heart failure, cerebrovascular spasm mostly after subarachnoid hemorrhage, cerebroischemic disturbance, urinary incontinence, benign prostatic hypertrophy, arteriosclerosis, Raynaud's syndrome, diabetic peripheral circulatory disturbance, diabetic renal diseases, preeclampsia, premature delivery, digestive ulcer, hepatic failure, rheumatism, restenosis after PTCA, chronic respiratory failure, chronic obstructive pulmonary diseases, cor pulmonale, acute respiratory failure, pulmonary edema, ischemic hepatic disturbance, adult respiratory distress syndrome, interstitial pneumonia, pulmonary fibrosis, glaucoma, osteoarthritis, chronic articular rheumatism, hepatic cirrhosis, inflammatory bowel diseases and cancer.

In addition, the compounds of the present invention show excellent absorption per os and, further, their sustaining property is good as well.

Action of the compounds of the present invention was ascertained by the following pharmacological tests.

(1) Test on Inhibition of Binding of Endothelin (ET-1) to Human $ET_A$ Receptor (Operating Method)

cDNA of human $ET_A$ receptor was obtained from mRNA of human lung by means of an RT-PCR and then transferred into pEF-BOS, a vector for expression, to prepare plasmid. The prepared plasmid was added to a culture of COS-1 cells (cell strain derived from renal cells of African green monkey) with DEAE-dextran and cDNA of human $ET_A$ was transfected to COS-1 cells. Then it was incubated for three days in a conventional DMEM (containing 10% of FBS) and the COS-1 cells recovered therefrom were suspended in a hypotonic buffer (10 mM Tris-HCl and 5 mM EDTA; pH 7.4) followed by homogenizing the cells using a Polytron. The suspension in which the cells were homogenized was subjected to an ultracentrifugation (100,000G for 30 minutes at 4° C.), the resulting precipitate (cell membrane fraction) was re-suspended in a Tris buffer (50 mM Tris-HCl and 10 mM $MgCl_2$; pH 7.4) and the suspension was preserved by freezing at −80° C. (protein amount: about 1 mg/ml).

In conducting the experiment of binding the receptor, the frozen cell membrane sample was melted and resuspended in an incubation buffer (50 mM Tris-HCl, 10 mM $MgCl_2$ and 0.01% bovine serum albumin; pH 7.4). The membrane suspension (200 μl) containing 1.25 μg as a membrane protein, 25 μl of an incubation buffer containing a test compound in various concentrations and 25 μl of [$^{125}$I] ET-1 (specific activity: 2,200 Ci/mM; final concentration: 25 μM) were incubated together at 25° C. for three hours and then filtered through a glass fiber filter using a Brandel cell harvester. Measurement of radioactivity on the glass fiber filter was conducted by means of a gamma-counter (counting efficiency: 81%). Nonspecific binding was determined by the use of a test buffer containing 0.1 μM of ET-1. Inhibiting activity of the test compound to [$^{125}$I] ET-1 was calculated as a concentration ($IC_{50}$) necessary for inhibiting 50% of the specific binding.

(Results)

The compounds of the present invention strongly suppressed the binding of ET-1 to human $ET_A$ receptor. The result is shown in the following table.

TABLE 1

| Tested Compound | $IC_{50}$ (nM) |
| --- | --- |
| Example 1 | 1.6 |
| Example 2 | 3.1 |
| Example 6 | 4.8 |
| Example 8 | 2.9 |
| Example 13 | 5.5 |
| Example 22 | 9.5 |
| Example 27 | 5.9 |
| Example 32 | 5.1 |
| Example 33 | 7.7 |
| Example 34 | 9.7 |
| Example 37 | 1.6 |
| Example 38 | 3.3 |
| Example 39 | 2.8 |
| Example 42 | 1.5 |

TABLE 1-continued

| Tested Compound | IC$_{50}$ (nM) |
|---|---|
| Example 45 | 4.4 |
| Example 47 | 3.0 |

(2) Test on Inhibition of Contraction Induced by ET-1 in Ring Preparation Sample of Rat Aorta
(Operating Method)

Ring preparations having a length of 2 mm were prepared from thoracic aorta of male Wistar rats (body weight: 300 to 350 g). Internal cavity of the ring was lightly rubbed by sanitary cotton to remove the endothelium. Each of the ring preparations was mounted with a resting tension of 1 g in an organ bath filled with 10 ml of a Krebs-Henseleit solution bubbled with 95% of $CO_2$ and 5% of $O_2$. The tension generated from the ring preparation was recorded isometrically. After incubating for ten minutes together with a test compound, ET-1 was added to the organ bath in a cumulative manner. The antagonistic activity of the test compound to ET-1 receptor was calculated as a concentration (pA$_2$) of the test compound necessary for transferring the ET-1 concentration-response curve two-fold to the right hand direction from the width (dose ratio) of transfer to the right hand direction of the concentration-response curve of ET-1 of the test compound of various concentrations.

(Results)

The compounds of the present invention strongly suppressed the contraction which was induced by ET-1 in artery ring sample of rats.

(3) Test on Inhibition of Big ET-1-induced Pressor Responses in Pithed Rats
(Operating Method)

Male Wistar rats (body weight: 25–350 g) were anesthetized by sodium pentobarbital (60 mg/kg, i.p.) and a cannula for artificial ventilation was inserted into a trachea. Spinal cord was broken by inserting a rod made of steel thereinto and then the rat was connected to an artificial respirator. A catheter for measuring the systemic arterial blood pressure was inserted into a carotid artery while another catheter for administering big ET-1 was inserted into a femoral vein. After 30 minutes from the oral administration of a test compound at doses of 0.1 to 10 mg/kg, the rat was pithed and then big ET-1 was intravenously administered at doses of 0.1 to 3.2 nmol/kg in a cumulative manner. Activity of the test compound was evaluated by the dose (DR$_2$ value) whereby the dose-response curve of pressor responses by big ET-1 to the right hand direction to an extent of two-fold.

(Results)

Oral administration of the compounds of the present invention exhibited an excellent suppressive action to big ET-1-induced pressor responses in pithed rats. The results are shown in the following Table.

TABLE 2

| Tested Compound | DR$_2$ (mg/kg) |
|---|---|
| Example 2 | 0.61 |
| Example 38 | 0.65 |
| Example 42 | 1.85 |
| Comparative Compound* | 32 |

*Comparative Compound: a compound mentioned in Example 67 of the Japanese Laid-Open Patent Publication Hei-05/222,003 (generic name: Bosentan)

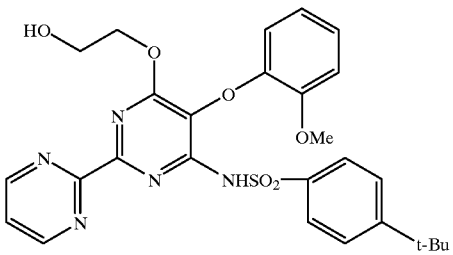

(4) Test on Inhibition of Big ET-1-induced Pressor Responses in Conscious Rats

Male Wistar rats (body weight: 250 to 350 g) were anesthetized by sodium pentobarbital (60 mg/kg, i.p.). A catheter for measuring the systemic arterial blood pressure was inserted into a carotid artery while another catheter for administering big ET-1 was inserted into a jugular vein. Experiment was conducted after two to three days from the operation. Thus, big ET-1 was intravenously administered to conscious rats at a dose of 0.5 nmol/kg every one hour. After 30 minutes from the third administration of big ET-1, a test compound was orally administered at doses of 0.3 to 3 mg/kg. Activity of the test compound was evaluated by an inhibition of big ET-1-induced pressor responses.

(Results)

As a result of the test, the compounds of the present invention exhibited an excellent suppressive action to big ET-1-induced pressor responses in conscious rats.

A pharmaceutical composition containing the compound of the present invention (I) or salts thereof and a pharmaceutically acceptable carrier can be prepared by a commonly-used method from one or more of the compound represented by a formula (I) or a salt thereof and pharmaceutical carrier, filler and other additives which are commonly used for preparing a pharmaceutical preparation. Administration may be either by oral administration using tablets, pills, capsules, granules, powder and liquid or by parenteral administration using intravenous or intramuscular injections, suppositories and percutaneous agents.

With regard to a solid composition for oral administration according to the present invention, tablets, powder, granules, etc. are used. In such a solid composition, one or more active substance(s) is/are mixed with at least one inert diluent such as lactose, mannitol, glucose, hydroxypropylcellulose, microcrystalline cellulose, starch, polyvinylpyrrolidone and magnesium metasilicate aluminate. The composition may also contain additive(s) other than the inert diluent such as lubricant (e.g. magnesium stearate, disintegrating agent (e.g. calcium cellulose glycolate), stabilizer (e.g. lactose) and auxiliary solubilizer (e.g. glutamic acid and aspartic acid). Tablets and pills may, if necessary be coated with sugar coat or gastric or enteric film such as sucrose, gelatin, hydroxypropylcellulose and hydroxypropylmethyl-cellulose phthalate.

The liquid composition for oral administration includes pharmaceutically acceptable emulsions, solutions, suspensions, syrups, elixiers, etc. and contains commonly used inert diluents such as pure water and ethanol. Besides the inert diluents, the composition may also contain auxiliary agents such as moisturizers and suspending agents as well as sweeteners, seasoning agents, aromatic agents and antiseptics.

Injections for parenteral administration include aseptic aqueous or nonaqueous solutions, suspensions and emulsions. Aqueous solutions and suspensions contain, for example, distilled water for injections and a physiological saline solution. Nonaqueous solutions and suspensions contain, for example, propylene glycol, polyethylene glycol, plant oil such as olive oil, alcohols such as ethanol, Polysolvate 80 (trade name), etc. Such compositions may further contain auxiliary agents such as antiseptics, moisturizers, emulsifiers, dispersing agents, stabilizers (e.g. lactose) and auxiliary solubilizers (e.g. glutamic acid and aspartic acid). They can be made aseptic by means of, for example, filtration passing through a bacterial conserving filter, compounding with aseptic agent, or irradiation. They may also be used by manufacturing an aseptic solid composition followed by dissolving in aseptic water or aseptic solvent for injection before use.

In the case of oral administration, daily dose is usually from about 0.001 to 30 mg/kg body weight or, preferably, 0.1 to 5 mg/kg and this is administered at a time or by dividing into two to four times a day. In the case of an intravenous administration, an appropriate dose per day is from about 0.001 to 30 mg/kg body weigh and it is administered at a time or by dividing into two or more times a day. The dose may be suitably decided for each case by taking symptom, age, sex, etc. into consideration.

BEST MODE FOR CONDUCTING THE INVENTION

The present invention will be illustrated in more detail by means of the following examples. The compounds of the present invention are not limited to the compounds which are mentioned in the following examples only. Incidentally, the methods for the manufacture of the starting compounds used in the examples will be given as referential examples.

REFERENTIAL EXAMPLE 1

Sodium hydride (60%) (480 mg) was added to a solution of 1.00 g of 2-phenylethenesulfonamide in 10 ml of dimethylformamide with ice cooling followed by stirring at room temperature for 15 minutes. To this reaction solution was added 1.91 g of 4,6-dichloro-5-(2-methoxyphenoxy)-2-(2-pyrimidinyl)-pyrimidine with stirring. The reaction mixture was stirred at room temperature for 2.5 hours and poured into a mixture of 1N hydrochloric acid and ice. The resulting crystals were collected by filtration and pulverized in hot ethanol. After allowing to cool, the crystals were collected by filtration to give 1.91 g of N-[6-chloro-5-(2-methoxyphenoxy)-2-(2-pyrimidinyl)-4-pyrimidinyl]-2-phenylethenesulfonamide.

REFERENTIAL EXAMPLE 2

N-[6-Chloro-5-(2-methoxyphenoxy)-2-(2-pyrimidinyl)-4-pyrimidinyl]-2-(3-methylphenyl)ethenesulfonamide was prepared by the same manner as in Referential Example 1.

REFERENTIAL EXAMPLE 3

N-[6-Chloro-5-(4-methoxycarbonyl-2-propylphenoxy)-2-(2-pyrimidinyl)-4-pyrimidinyl]-2-phenylethenesulfonamide was prepared by the same manner as in Referential Example 1.

4,6-Dichloro-5-(4-methoxycarbonyl-2-propylphenoxy)-2-(2-pyrimidinyl)-pyrimidine which is a starting material for the above-prepared compound was synthesized as follows.

To 3.00 g of 4,6-dihydroxy-5-(4-methoxycarbonyl-2-propylphenoxy)-2-(2-pyrimidinyl)-pyrimidine were added 10 ml of phosphorus oxychloride and 1.2 ml of collidine and the mixture was heated to reflux for four hours with stirring. The reaction solution was poured into ice water followed by extracting with chloroform. The chloroform layer was washed with a saturated sodium chloride solution, dried over anhydrous magnesium sulfate and filtered. The filtrate was concentrated in vacuo and the crystals in the residue were pulverized in ether and collected by filtration to give 1.76 g of 4,6-dichloro-5-(4-methoxycarbonyl-2-propylphenoxy)-2-(2-pyrimidinyl)-pyrimidine.

The compounds of the following Referential Examples were synthesized by the same manner as in Referential Example 1.

REFERENTIAL EXAMPLE 4

N-[6-Chloro-5-(2-methoxyphenoxy)-2-trifluoromethyl-4-pyrimidinyl]-2-phenylethenesulfonamide.

REFERENTIAL EXAMPLE 5

N-[6-Chloro-2-cyclopropyl-5-(2-methoxyphenoxy)-4-pyrimidinyl]-2-phenylethenesulfonamide.

REFERENTIAL EXAMPLE 6

N-[6-Chloro-5-(2-methoxyphenoxy)-2-phenyl-4-pyrimidinyl]-2-phenylethenesulfonamide.

REFERENTIAL EXAMPLE 7

N-[6-Chloro-5-(2-methoxyphenoxy)-2-(4-trifluoromethylphenyl)-4-pyrimidinyl]-2-phenylethenesulfonamide.

REFERENTIAL EXAMPLE 8

N-[6-Chloro-5-(2-methoxyphenoxy)-2-(3-nitrophenyl)-4-pyrimidinyl]-2-phenylethenesulfonamide.

REFERENTIAL EXAMPLE 9

N-[6-Chloro-2-(3,5-dimethoxyphenyl)-5-(2-methoxyphenoxy)-4-pyrimidinyl]-2-phenylethenesulfonamide.

REFERENTIAL EXAMPLE 10

N-[6-Chloro-5-(2-methoxyphenoxy)-2-(3-methoxyphenyl)-4-pyrimidinyl]-2-phenylethenesulfonamide.

REFERENTIAL EXAMPLE 11

N-[6-Chloro-5-(2-methoxyphenoxy)-2-(3,4-methylenedioxyphenyl)-4-pyrimidinyl]-2-phenylethenesulfonamide.

REFERENTIAL EXAMPLE 12

N-[6-Chloro-5-(2-methoxyphenoxy)-2-(3,4,5-trimethoxyphenyl)-4-pyrimidinyl]-2-phenylethenesulfonamide.

REFERENTIAL EXAMPLE 13

N-[6-Chloro-5-(2-methoxyphenoxy)-2-(2-pyridyl)-4-pyrimidinyl]-2-phenylethenesulfonamide.

REFERENTIAL EXAMPLE 14

N-[6-Chloro-5-(2-methoxyphenoxy)-2-(4-pyridyl)-4-pyrimidinyl]-2-phenylethenesulfonamide.

REFERENTIAL EXAMPLE 15

N-[6-Chloro-5-(2-methoxyphenoxy)-2-(3-pyridyl)-4-pyrimidinyl]-2-phenylethenesulfonamide.

REFERENTIAL EXAMPLE 16

N-[6-Chloro-2-(6-chloro-3-pyridyl)-5-(2-methoxyphenoxy)-4-pyrimidinyl]-2-phenylethenesulfonamide.

REFERENTIAL EXAMPLE 17

N-[6-Chloro-5-(2-methoxyphenoxy)-2-(6-trifluoromethyl-3-pyridyl)-4-pyrimidinyl]-2-phenylethenesulfonamide.

REFERENTIAL EXAMPLE 18

N-[6-Chloro-5-(2-methoxyphenoxy)-2-(2-thienyl)-4-pyrimidinyl]-2-phenylethenesulfonamide.

REFERENTIAL EXAMPLE 19

N-[6-Chloro-5-(2-methoxyphenoxy)-2-(3-thienyl)-4-pyrimidinyl]-2-phenylethenesulfonamide.

REFERENTIAL EXAMPLE 20

N-[6-Chloro-5-(2-methoxyphenoxy)-2-(2-methyl-4-thiazolyl)-4-pyrimidinyl]-2-phenylethenesulfonamide.

REFERENTIAL EXAMPLE 21

N-[6-Chloro-2-(3-furyl-5-(2-methoxyphenoxy)-4-pyrimidinyl]-2-phenylethenesulfonamide.

REFERENTIAL EXAMPLE 22

N-[6-Chloro-5-(2-methoxyphenoxy)-2-(2-pyrimidinyl)-4pyrimidinyl]-1-methyl-2-phenylethenesulfonamide.

REFERENTIAL EXAMPLE 23

N-[6-Chloro-5-(2-methoxyphenoxy)-2-(2-pyrimidinyl)-4-pyrimidinyl]-1-ethyl-2-phenylethenesulfonamide.

REFERENTIAL EXAMPLE 24

N-[6-Chloro-5-(2-methoxyphenoxy)-2-(2-pyrimidinyl)-4-pyrimidinyl]-2-(4-methylphenyl)ethenesulfonamide.

REFERENTIAL EXAMPLE 25

N-[6-Chloro-5-(2-methoxyphenoxy)-2-(2-pyrimidinyl)-4-pyrimidinyl]-2-(4-tert-butylphenyl)ethenesulfonamide.

REFERENTIAL EXAMPLE 26

N-[6-Chloro-5-(2-methoxyphenoxy)-2-(2-pyrimidinyl)-4-pyrimidinyl]-2-(4-chlorophenyl)ethenesulfonamide.

REFERENTIAL EXAMPLE 27

N-[6-Chloro-5-(2-methoxyphenoxy)-2-(2-pyrimidinyl)-4-pyrimidinyl]-2-(2-thienyl)ethenesulfonamide.

REFERENTIAL EXAMPLE 28

N-[6-Chloro-5-(2-methoxyphenoxy)-2-(2-pyrimidinyl)-4-pyrimidinyl]-2-(4-trifluorophenyl)ethenesulfonamide.

REFERENTIAL EXAMPLE 29

N-[6-Chloro-5-(2-methoxyphenoxy)-2-(2-pyrimidinyl)-4-pyrimidinyl]-2-(4-methoxyphenyl)ethenesulfonamide.

REFERENTIAL EXAMPLE 30

N-[6-Chloro-5-(2-methoxyphenoxy)-2-(2-pyrimidinyl)-4-pyrimidinyl]-2-(2-naphthyl)ethenesulfonamide.

REFERENTIAL EXAMPLE 31

N-[6-Chloro-5-(2-methoxyphenoxy)-2-(2-pyrimidinyl)-4-pyrimidinyl]-2-(1-naphthyl)ethenesulfonamide.

REFERENTIAL EXAMPLE 32

N-[6-Chloro-5-(2-methoxyphenoxy)-2-(2-pyrimidinyl)-4-pyrimidinyl]-2-(2-chlorophenyl)ethenesulfonamide.

REFERENTIAL EXAMPLE 33

N-[6-Chloro-5-(2-methoxyphenoxy)-2-(2-pyrimidinyl)-4-pyrimidinyl]-2-(4-methoxycarbonylphenyl)ethenesulfonamide.

REFERENTIAL EXAMPLE 34

N-[6-Chloro-5-(2-methoxyphenoxy)-2-(2-pyrimidinyl)-4-pyrimidinyl]-2-(3-thienyl)ethenesulfonamide.

REFERENTIAL EXAMPLE 35

N-[6-Chloro-5-(2-methoxyphenoxy)-2-(2-pyrimidinyl)-4-pyrimidinyl]-2-(3-chlorophenyl)ethenesulfonamide.

REFERENTIAL EXAMPLE 36

N-[6-Chloro-5-(2-methoxyphenoxy)-2-(2-pyrimidinyl)-4-pyrimidinyl]-2-phenyl-1-propylethenesulfonamide.

REFERENTIAL EXAMPLE 37

N-[6-Chloro-5-(2-methoxyphenoxy)-2-(2-pyrimidinyl)-4-pyrimidinyl]-2-methyl-2-phenylethenesulfonamide.

REFERENTIAL EXAMPLE 38

N-[6-Chloro-5-(2-methoxyphenoxy)-2-(2-pyrimidinyl)-4-pyrimidinyl]-2-(2-methylphenyl)ethenesulfonamide.

REFERENTIAL EXAMPLE 39

N-[6-Chloro-5-(2-methoxyphenoxy)-2-(2-pyrimidinyl)-4-pyrimidinyl]-2-(2,4,6-trimethylphenyl)ethenesulfonamide.

EXAMPLE 1

Sodium (230 mg) was dissolved in 5.6 ml of ethylene glycol and 495 mg of N-[6-chloro-5-(2-methoxyphenoxy)-2-(2-pyrimidinyl)-4-pyrimidinyl]-2-phenylethenesulfonamide was added thereto under ice cooling with stirring. The reaction mixture was stirred at 80° C. for three hours and poured into a mixture of 1N hydrochloric acid and ice. The crystals separated out therefrom were collected by filtration and the resulting crystals were purified by a silica gel column chromatography (chloroform-methanol=20:1) to give 500 mg of N-[6-(2-hydroxyethoxy)-5-(2-methoxyphenoxy)-2-(2-pyrimidinyl)-4-pyrimidinyl]-2-phenylethenesulfonamide.

To a methanolic solution of 104 mg of the resulting sulfonamide derivative was added 2 ml of 0.1N ethanolic KOH solution followed by concentrating in vacuo. The resulting solid was pulverized in ether and collected by filtration to give 84 mg of potassium N-[6-(2-hydroxyethoxy)-5-(2-methoxyphenoxy)-2-(2-pyrimidinyl)-4-pyrimidinyl]-2-phenylethenesulfonamidate.

EXAMPLE 2

Sodium (181 mg) was dissolved in 10 ml of methanol and 400 mg of N-[6-chloro-5-(2-methoxyphenoxy)-2-(2- pyrimidinyl)-4-pyrimidinyl]-2-phenylethenesulfonamide was added with stirring at room temperature. The reaction mixture was stirred at room temperature for three hours and poured into a mixture of 1N hydrochloric acid and ice. The crystals separated out therefrom were collected by filtration and the resulting crystals were purified by a silica gel column chromatography (chloroform-methanol=40:1). The resulting yellow amorphous substance was crystallized in ether and collected by filtration to give 273 mg of N-[6-methoxy-5-(2-methoxyphenoxy)-2-(2-pyrimidinyl)-4-pyrimidinyl]-2-phenylethenesulfonamide.

Compounds of the following Examples 3 to 6 were prepared by the same manner as in Example 2.

EXAMPLE 3

N-[6-ethoxy-5-(2-methoxyphenoxy)-2-(2-pyrimidinyl)-4-pyrimidinyl]-2-phenylethenesulfonamide.

EXAMPLE 4

N-[5-(2-Methoxyphenoxy)-6-propoxy-2-(2-pyrimidinyl)-4-pyrimidinyl]-2-phenylethenesulfonamide.

EXAMPLE 5

N-[6-Cyclopropylmethoxy-5-(2-methoxyphenoxy)-2-(2-pyrimidinyl)-4-pyrimidinyl]-2-phenylethenesulfonamide.

EXAMPLE 6

N-[6-(2-Methoxyethoxy)-5-(2-methoxyphenoxy)-2-(2-pyrimidinyl)-4-pyrimidinyl]-2-phenylethenesulfonamide.

EXAMPLE 7

Sodium (181 mg) was added to 10 ml of isopropyl alcohol and, after one hour, 100 ml of isopropyl alcohol was added thereto followed by heating at 60° C. to dissolve. To this reaction solution was added 400 mg of N-[6-chloro-5-(2-methoxyphenoxy)-2-(2-pyrimidinyl)-4-pyrimidinyl]-2-phenylethenesulfonamide with stirring at room temperature. The reaction mixture was stirred at room temperature for 1.25 hours and then at 60° C. for 45 minutes followed by pouring into a mixture of 1N hydrochloric acid and ice. The solution was extracted with chloroform and the chloroform layer was dried over anhydrous magnesium sulfate followed by filtering. The filtrate was concentrated in vacuo and the resulting residue was purified by a silica gel column chromatography (ethyl acetate). The resulting amorphous substance was crystallized in ether and collected by filtration to give 57 mg of N-[6-isopropoxy-5-(2-methoxyphenoxy)-2-(2-pyrimidinyl)-4-pyrimidinyl]-2-phenylethenesulfonamide.

EXAMPLE 8

To a solution of 258 mg of fluoroethanol in 20 ml of dimethylformamide was added 194 mg of sodium hydride (60%) with ice cooling followed by stirring for 30 minutes. To this reaction solution was added 400 mg of N-[6-chloro-5-(2-methoxyphenoxy)-2-(2-pyrimidinyl)-4-pyrimidinyl]-2-phenylethenesulfonamide with stirring under ice cooling followed by stirring for 30 minutes. The reaction mixture was stirred at room temperature for two hours and poured into a mixture of 1N hydrochloric acid and ice. This solution was extracted with chloroform and the chloroform layer was dried over anhydrous magnesium sulfate and filtered. The filtrate was concentrated in vacuo and the resulting residue was purified by a silica gel column chromatography (chloroform-methanol=40:1). The resulting amorphous substance was crystallized in ether and collected by filtration to give 240 mg of N-[6-(2-fluoroethoxy)-5-(2-methoxyphenoxy)-2-(2-pyrimidinyl)-4-pyrimidinyl]-2-phenylethenesulfonamide.

Compounds of the following Examples 9 to 10 were prepared by the same manner as in Example 8.

EXAMPLE 9

N-[6-(2,2-Difluoroethoxy)-5-(2-methoxyphenoxy)-2-(2-pyrimidinyl)-4-pyrimidinyl]-2-phenylethenesulfonamide.

EXAMPLE 10

N-[5-(2-Methoxyphenoxy)-2-(2-pyrimidinyl)-6-(2,2,2-trifluoroethoxy)-4-pyrimidinyl]-2-phenylethenesulfonamide.

EXAMPLE 11

Sodium (693 mg) was added to and dissolved in 18.2 ml of aminoethanol. To this reaction solution was added 3.00 g of N-[6-chloro-5-(2-methoxyphenoxy)-2-(2-pyrimidinyl)-4-pyrimidinyl]-2-phenylethenesulfonamide with stirring at room temperature. The reaction mixture was stirred at 60° C. for one hour and then at 80° C. for two hours followed by pouring into a mixture of 1N hydrochloric acid and ice. This solution was neutralized with a saturated sodium bicarbonate solution and extracted with ethyl acetate and the ethyl acetate layer was dried over anhydrous magnesium sulfate and filtered. The filtrate was concentrated in vacuo and the resulting residue was purified by a silica gel column chromatography (chloroform-methanol=20:1). The resulting amorphous substance was pulverized in ether and collected by filtration to give 2.40 g of N-[6-(2-hydroxyethylamino)-5-(2-methoxyphenoxy)-2-(2-pyrimidinyl)-4-pyrimidinyl]-2-phenylethenesulfonamide.

EXAMPLE 12

Sodium (1.031 g) was dissolved in 20.130 g of 1,3-propanediol and 2.091 g of N-[6-chloro-5-(2-methoxyphenoxy)-2-(2-pyrimidinyl)-4-pyrimidinyl]-2-phenylethenesulfonamide was added thereto with stirring at room temperature. The reaction mixture was stirred at room temperature for 50 minutes and then at 60° C. for 50 minutes and poured into a mixture of 1N hydrochloric acid and ice. This was extracted with ethyl acetate and the ethyl acetate layer was dried over anhydrous magnesium sulfate and filtered. The filtrate was concentrated in vacuo and the resulting residue was purified by a silica gel column chromatography (chloroform-methanol=100:1 to 20:1). The resulting syrup was crystallized in ether and collected by filtration to give 1.817 g of N-[6-(3-hydroxypropyloxy)-5-(2-methoxyphenoxy)-2-(2-pyrimidinyl)-4-pyrimidinyl]-2-phenylethenesulfonamide.

EXAMPLE 13

Sodium (185 mg) was dissolved in 5 ml of 2-propyn-1-ol and 390 mg of N-[6-chloro-5-(2-methoxyphenoxy)-2-(2-pyrimidinyl)-4-pyrimidinyl]-2-phenylethenesulfonamide was added thereto with stirring at room temperature. The reaction mixture was stirred at 60° C. for one hour and poured into a mixture of 1N hydrochloric acid and ice. This was extracted with ethyl acetate and the ethyl acetate layer was dried over anhydrous magnesium sulfate and filtered. The filtrate was concentrated in vacuo and the resulting residue was purified by a silica gel column chromatography (chloroform-methanol=100:1 to 30:1). The resulting syrup was crystallized in ether and collected filtration to give 342 mg of N-[6-(2-propynyloxy)-5-(2-methoxyphenoxy)-2-(2-pyrimidinyl)-4-pyrimidinyl]-2-phenylethenesulfonamide.

EXAMPLE 14

Sodium (315 mg) was dissolved in 7.7 ml of ethylene glycol and 700 mg of N-[6-chloro-5-(2-methoxyphenoxy)-2-(2-pyrimidinyl)-4-pyrimidinyl]-2-(3-methylphenyl)ethenesulfonamide was added thereto with stirring. The reaction mixture was stirred at 90° C. for 30 minutes and poured into a mixture of 1N hydrochloric acid and ice. Crystals separated out therefrom were collected by filtration and the resulting crystals were purified by a silica gel column chromatography (chloroform-methanol=20:1). The resulting amorphous substance was crystallized in ether and collected filtration to give 533 mg of N-[6-(2-hydroxyethoxy)-5-(2-methoxyphenoxy)-2-(2-pyrimidinyl)-4-pyrimidinyl]-2-(3-methylphenyl)ethenesulfonamide.

EXAMPLE 15

(a) To 508 mg of N-[6-methoxy-5-(2-methoxyphenoxy)-2-(2-pyrimidinyl)-4-pyrimidinyl]-2-phenylethenesulfonamide was added 10.3 ml of ethanolic 0.1M potassium hydroxide solution followed by stirring overnight. Crystals separated out therefrom were collected by filtration and recrystallized from ethanol-water to give 330 mg of potassium N-[6-methoxy-5-(2-methoxyphenoxy)-2-(2-pyrimidinyl)-4-pyrimidinyl]-2-phenylethenesulfonamidate.

(b) To 1.00 g of N-[6-methoxy-5-(2-methoxyphenoxy)-2-(2-pyrimidinyl)-4-pyrimidinyl]-2-phenylethenesulfonamide were added 10 ml of ethanol-water (4:1) and 110 mg of sodium methoxide followed by heating to reflux. To this was added 18 ml of ethanol-water (4:1) so that the crystals were completely dissolved. This was filtered when hot, the filtrate was stirred at room temperature and the crystals separated out therefrom were collected by filtration. The crystals were washed with ethanol-water (4:1) to give 80 mg of sodium N-[6-methoxy-5-(2-methoxyphenoxy)-2-(2-pyrimidinyl)-4-pyrimidinyl]-2-phenylethenesulfonamidate monohydrate.

EXAMPLE 16

Sodium (356 mg) was dissolved in 20 ml of methanol and 900 mg of N-[6-chloro-5-(4-methoxycarbonyl-2-propylphenoxy)-2-(2-pyrimidinyl)-4-pyrimidinyl]-2-phenylethenesulfonamide was added thereto with stirring at room temperature. The reaction mixture was stirred at room temperature for five hours and forty minutes, at 60° C. for one hour and fifty minutes and at room temperature overnight. After that, the mixture was poured into a mixture of IN hydrochloric acid and ice. Crystals separated out therefrom were collected by filtration and the resulting crystals were purified by a silica gel column chromatography (chloroform-ethanol=20:1). The resulting amorphous substance was crystallized in ether and collected by filtration to give 452 mg of N-[6-methoxy-5-(4-methoxycarbonyl-2-propylphenoxy)-2-(2-pyrimidinyl)-4-pyrimidinyl]-2-phenylethenesulfonamide.

EXAMPLE 17

Sodium methoxide (336 mg) was added to a solution of 320 mg of N-[6-chloro-5-(2-methoxyphenoxy)-2-trifluoromethyl-4-pyrimidinyl]-2-phenylethenesulfonamide in 10 ml of N,N-dimethylformamide followed by stirring overnight. The reaction mixture was poured into a mixture of ice and 1N hydrochloric acid and the solid separated out therefrom was collected by filtration. This solid was purified by a silica gel column chromatography (chloroform) and the resulting oil was crystallized from ether to give 210 mg of N-[6-methoxy-5-(2-methoxyphenoxy)-2-trifluoromethyl-4-pyrimidinyl]-2-phenylethenesulfonamide.

Compounds of the following Examples 18 to 25 were prepared by the same manner as in Example 17 except that, if necessary, the reaction was conducted at room temperature or by heating up to the temperature of 110° C. Incidentally, the compound forming a salt was synthesized by subjecting to the same salt-forming reaction as in Example 15.

EXAMPLE 18

Potassium N-[2-cyclopropyl-6-methoxy-5-(2-methoxyphenoxy)-4-pyrimidinyl]-2-phenylethenesulfonamidate.

EXAMPLE 19

N-[6-Methoxy-5-(2-methoxyphenoxy)-2-phenyl-4-pyrimidinyl]-2-phenylethenesulfonamide.

EXAMPLE 20

N-[6-Methoxy-5-(2-methoxyphenoxy)-2-(4-trifluoromethylphenyl)-4-pyrimidinyl]-2-phenylethenesulfonamide.

EXAMPLE 21

N-[6-Methoxy-5-(2-methoxyphenoxy)-2-(3-nitrophenyl)-4-pyrimidinyl]-2-phenylethenesulfonamide.

EXAMPLE 22

N-[2-(3,5-Dimethoxyphenyl)-6-methoxy-5-(2-methoxyphenoxy)-4-pyrimidinyl]-2-phenylethenesulfonamide.

EXAMPLE 23

N-[6-Methoxy-5-(2-methoxyphenoxy)-2-(3-methoxyphenyl)-4-pyrimidinyl]-2-phenylethenesulfonamide.

EXAMPLE 24

N-[6-Methoxy-5-(2-methoxyphenoxy)-2-(3,4-methylenedioxyphenyl)-4-pyrimidinyl]-2-phenylethenesulfonamide.

EXAMPLE 25

N-[6-Methoxy-5-(2-methoxyphenoxy)-2-(3,4,5-trimethoxyphenyl)-4-pyrimidinyl]-2-phenylethenesulfonamide.

Compounds of the following Examples 26 to 27 were prepared by the same manner as in Example 2.

EXAMPLE 26

N-[6-Methoxy-5-(2-methoxyphenoxy)-2-(2-pyridyl)-4-pyrimidinyl]-2-phenylethenesulfonamide.

EXAMPLE 27

N-[6-Methoxy-5-(2-methoxyphenoxy)-2-(4-pyridyl)-4-pyrimidinyl]-2-phenylethenesulfonamide.

Compounds of the following Examples 28 to 29 were prepared by the same manner as in Example 17 except that, if necessary, the reaction was conducted at room temperature or by heating up to 110° C.

EXAMPLE 28

N-[6-Methoxy-5-(2-methoxyphenoxy)-2-(3-pyridyl)-4-pyrimidinyl]-2-phenylethenesulfonamide.

EXAMPLE 29

N-[6-Methoxy-5-(2-methoxyphenoxy)-2-(6-methoxy-3-pyridyl)-4-pyrimidinyl]-2-phenylethenesulfonamide.

EXAMPLE 30

N-[6-Methoxy-5-(2-methoxyphenoxy)-2-(6-trifluoromethyl-3-pyridyl)-4-pyrimidinyl]-2-phenylethenesulfonamide was prepared by the same manner as in Example 2.

Compounds of the following Examples 31 to 34 were prepared by the same manner as in Example 17 except that, if necessary, the reaction was conducted at room temperature or by heating up to 110° C.

EXAMPLE 31

N-[6-Methoxy-5-(2-methoxyphenoxy)-2-(2-thienyl)-4-pyrimidinyl]-2-phenylethenesulfonamide.

EXAMPLE 32

N-[6-Methoxy-5-(2-methoxyphenoxy)-2-(3-thienyl)-4-pyrimidinyl]-2-phenylethenesulfonamide.

EXAMPLE 33

N-[6-Methoxy-5-(2-methoxyphenoxy)-2-(2-methyl-4-thiazolyl)-4-pyrimidinyl]-2-phenylethenesulfonamide.

EXAMPLE 34

N-[6-Methoxy-5-(2-methoxyphenoxy)-2-(3-furyl)-4-pyrimidinyl]-2-phenylethenesulfonamide.

EXAMPLE 35

N-[5-(2-Methoxyphenoxy)-6-(2-propynyloxy)-2-(6-trifluoromethyl-3-pyridyl)-4-pyrimidinyl]-2-phenylethenesulfonamide was prepared by the same manner as in Example 13.

EXAMPLE 36

N-[6-(2-Hydroxyethoxy)-5-(2-methoxyphenoxy)-2-(6-trifluoromethyl-3-pyridyl)-4-pyrimidinyl]-2-phenylethenesulfonamide was prepared by the same manner as in Example 1.

Compounds of the following Examples 37 to 42 were prepared by the same manner as in Example 17 except that, if necessary, the reaction was conducted at room temperature or by heating up to 110° C. Incidentally, a compound forming a salt was synthesized by subjecting to a further salt-forming reaction by the same manner as in Example 15.

EXAMPLE 37

N-[6-Methoxy-5-(2-methoxyphenoxy)-2-(2-pyrimidinyl)-4-pyrimidinyl]-1-methyl-2-phenylethenesulfonamide.

EXAMPLE 38

Potassium N-[6-methoxy-5-(2-methoxyphenoxy)-2-(2pyrimidinyl)-4-pyrimidinyl]-1-ethyl-2-phenylethenesulfonamidate.

EXAMPLE 39

N-[6-Methoxy-5-(2-methoxyphenoxy)-2-(2-pyrimidinyl)-4-pyrimidinyl]-2-(4-methylphenyl)ethenesulfonamide.

EXAMPLE 40

Potassium N-[6-methoxy-5-(2-methoxyphenoxy)-2-(2-pyrimidinyl)-4-pyrimidinyl]-2-(4-tert-butylphenyl)ethenesulfonamidate.

EXAMPLE 41

N-[6-Methoxy-5-(2-methoxyphenoxy)-2-(2-pyrimidinyl)-4-pyrimidinyl]-2-(4-chlorophenyl)ethenesulfonamide.

EXAMPLE 42

N-[6-Methoxy-5-(2-methoxyphenoxy)-2-(2-pyrimidinyl)-4-pyrimidinyl]-2-(2-thienyl)ethenesulfonamide.

Compounds of the following Examples 43 to 48 were prepared by the same manner as in Example 2. Incidentally, a compound forming a salt was synthesized by subjecting to the same salt-forming reaction as in Example 15.

EXAMPLE 43

Potassium N-[6-methoxy-5-(2-methoxyphenoxy)-2-(2-pyrimidinyl)-4-pyrimidinyl]-2-(4-trifluorophenyl)ethenesulfonamidate.

EXAMPLE 44

N-[6-Methoxy-5-(2-methoxyphenoxy)-2-(2-pyrimidinyl)-4-pyrimidinyl]-2-(4-methoxyphenyl)ethenesulfonamide.

EXAMPLE 45

N-[6-Methoxy-5-(2-methoxyphenoxy)-2-(2-pyrimidinyl)-4-pyrimidinyl]-2-(2-naphthyl)ethenesulfonamide.

EXAMPLE 46

N-[6-Methoxy-5-(2-methoxyphenoxy)-2-(2-pyrimidinyl)-4-pyrimidinyl]-2-(1-naphthyl)ethenesulfonamide.

EXAMPLE 47

N-[6-Methoxy-5-(2-methoxyphenoxy)-2-(2-pyrimidinyl)-4-pyrimidinyl]-2-(2-chlorophenyl)ethenesulfonamide.

EXAMPLE 48

N-[6-Methoxy-5-(2-methoxyphenoxy)-2-(2-pyrimidinyl)-4-pyrimidinyl]-2-(4-carboxyphenyl)ethenesulfonamide.

EXAMPLE 49

Concentrated sulfuric acid (0.1 ml) was added to a solution of 150 mg of N-[6-methoxy-5-(2-methoxyphenoxy)-2-(2-pyrimidinyl)-4-pyrimidinyl]-2-(4-carboxyphenyl)ethenesulfonamide in 10 ml of methanol followed by stirring overnight under a refluxing condition. The reaction mixture was concentrated in vacuo, 1N hydrochloric acid was added thereto and the mixture was extracted with ethyl acetate. The extract was washed with a saturated saline solution, dried over anhydrous sodium sulfate, filtered and concentrated in vacuo and the resulting solid was recrystallized form ethyl acetate to give 102 mg of N-[6-methoxy-5-(2-methoxyphenoxy)-2-(2-pyrimidinyl)-4-pyrimidinyl]-2-(4-methoxycarbonylphenyl)ethenesulfon-amide.

Compounds of the following Examples 50 to 51 were prepared by the same manner as in Example 2.

EXAMPLE 50

N-[6-Methoxy-5-(2-methoxyphenoxy)-2-(2-pyrimidinyl)-4-pyrimidinyl]-2-(3-thienyl)ethenesulfonamide.

EXAMPLE 51

N-[6-Methoxy-5-(2-methoxyphenoxy)-2-(2-pyrimidinyl)-4-pyrimidinyl]-2-(3-chlorophenyl)ethenesulfonamide.

EXAMPLE 52

Potassium N-[6-methoxy-5-(2-methoxyphenoxy)-2-(2-pyrimidinyl)-4-pyrimidinyl]-2-phenyl-1-propylethenesulfonamidate was prepared by the same manner as in Example 17 and Example 15(a).

Compounds of the following Examples 53 to 55 were prepared by the same manner as in Example 2.

EXAMPLE 53

N-[6-Methoxy-5-(2-methoxyphenoxy)-2-(2-pyrimidinyl)-4-pyrimidinyl]-2-methyl-2-phenylethenesulfonamide.

EXAMPLE 54

N-[6-Methoxy-5-(2-methoxyphenoxy)-2-(2-pyrimidinyl)-4-pyrimidinyl]-2-(2-methylphenyl)ethenesulfonamide.

EXAMPLE 55

N-[6-Methoxy-5-(2-methoxyphenoxy)-2-(2-pyrimidinyl)-4-pyrimidinyl]-2-(2,4,6-trimethylphenyl)ethenesulfonamide.

Structural formulae and physico-chemical properties of the compounds of the above Referential Examples are shown in Tables 3 to 4 and structural formulae and physico-chemical properties of the compounds of Examples are shown in Tables 5 to 8.

Abbreviations used in the tables have the following meanings.

Ref: Referential Example number
Ex.: Example number
Sa: salt
mp.: melting point
NMR: Nucleomagnetic resonance (DMSO-$d_6$, TMS internal standard unless otherwise mentioned) δ:
ana: elementary analysis data
tho: theoretical value
fou: found value
m/z: mass analysis data (m/z)
N.P.: used in the next step without purification
Ph: phenyl group
Pmy: pyrimidinyl group
cPr: cyclopropyl group
nPr: n-propyl group
The: thienyl group
Naph: naphthyl group
tBu: tert-butyl group
Py: pyridyl group
Thi: thiazolyl group
Fur: furyl group
triMeO: trimethoxy group
diMeo: dimethoxy group
triMe: trimethyl group

TABLE 3

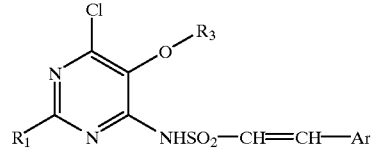

| Ref | R₃ | R₁ | Ar | |
|---|---|---|---|---|
| 1 | 2-MeO—Ph | 2-Pym | Ph | NMR: 3.80(3H, s), 6.83(1H, d), 6.86(1H, t), 7.11 (1H, t), 7.13(1H, d), 7.46(3H, m), 7.71–7.75(3H, m), 7.87(2H, m), 9.09(2H, d). |
| 2 | 2-MeO—Ph | 2-Pym | 3-Me—Ph | NMR: 2.32(3H, s), 3.80(3H, s), 6.82(1H, d), 6.87(1H, t), 7.09(1H, t), 7.13(1H, d), 7.26(1H, d), 7.33(1H, t), 7.52(2H, m), 7.73(1H, t) 7.85(2H, m), 9.09(2H, d). |
| 3 | 4-MeOOC-2-Pr—Ph | 2-Pym | Ph | NMR: 0.99(3H, t), 1.75(2H, m), 2.84(2H, m), 3.83(3H, s), 6.76(1H, d), 7.45(3H, m), 7.70–7.78(4H, m), 7.80–7.95(3H, m), 9.11(2H, d). |
| 4 | 2-MeO—Ph | —CF₃ | Ph | NMR: 3.79(3H, s), 6.84–6.90(2H, m), 7.06–7.14(2H, m), 7.41–7.49(4H, m), 7.65–7.74(3H, m). |
| 5 | 2-MeO—Ph | cPr | Ph | NMR: 0.92(2H, m), 0.99(2H, m), 2.08(1H, m), 3.81(3H, s), 6.62(1H, d), 6.84(1H, t), 7.05(1H, t), 7.11(1H, d), 7.44–7.48(4H, m), 7.64(1H, d), 7.74–7.76(2H, m), 11.60(1H, brs). |

TABLE 3-continued

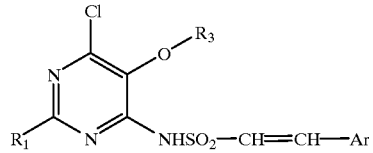

| Ref | R₃ | R₁ | Ar | |
|---|---|---|---|---|
| 6 | 2-MeO—Ph | Ph | Ph | NMR: 3.83(3H, s), 6.77(1H, m), 6.87(1H, m), 7.09(1H, m), 7.14(1H, m), 7.42–7.54(6H, m), 7.57(1H, d), 7.76–7.78(2H, m), 7.88(1H, d), 8.24–8.26(2H, m) 11.95(1H, brs). |
| 7 | 2-MeO—Ph | 4-CF₃—Ph | Ph | NMR: 3.82(3H, s), 6.81(1H, m), 6.87(1H, m), 7.07(1H, m), 7.14(1H, m), 7.41–7.43(3H, m), 7.56(1H, d), 7.78–7.80(2H, m), 7.85–7.91(3H, m), 8.44(2H, d). |
| 8 | 2-MeO—Ph | 3-NO₂—Ph | Ph | NMR: 3.83(3H, s), 6.82(1H, dd), 6.87(1H, dt), 7.09(1H, dt), 7.14(1H, dd), 7.38–7.44(3H, m), 7.57(1H, d), 7.72–7.75(2H, m), 7.82(1H, t), 7.88(1H, d), 8.39(1H, dd), 8.65 (1H, d), 8.99(1H, t). |
| 9 | 2-MeO—Ph | 3,5-diMeO—Ph | Ph | NMR: 3.80(6H, s), 3.63(3H, s), 6.69(1H, t), 6.79(1H, d), 6.87(1H, t), 7.09(1H, t), 7.14(1H, d), 7.40–7.47(5H, m), 7.56(1H, d), 7.68–7.72(2H, m), 7.79(1H, d). |
| 10 | 2-MeO—Ph | 3-MeO—Ph | Ph | NMR: 3.81(3H, s), 3.83(3H, s), 6.78(1H, dd), 6.87(1H, dt), 7.06–7.16(3H, m), 7.37–7.45(4H, m), 7.57(1H, d), 7.72–7.86(5H, m), 11.96(1H, brs). |
| 11 | 2-MeO—Ph | 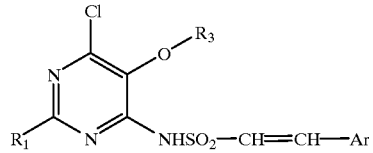 | Ph | NMR: 3.82(3H, s), 6.13(2H, 2), 6.75(1H, dd), 6.85(1H, dt), 7.01(1H, d), 7.07(1H, dt), 7.13(1H, dd), 7.40–7.47(3H, m), 7.55(1H, d), 7.66(1H, d), 7.74–7.77(2H, m), 7.83(1H, d), 7.86(1H, dd), 11.91(1H, brs) |
| 12 | 2-MeO—Ph | 3,4,5-tri MeO—Ph | Ph | NMR: 3.74(3H, s), 3.80(6H, s), 3.82(3H, s), 6.77(1H, dd), 6.87(1H, dt), 7.08(1H, dt), 7.13(1H, dd), 7.39–7.45 (3H, m), 7.57(2H, s), 7.59–7.66(3H, m), 7.74(1H, d). |
| 13 | 2-MeO—Ph | 2-Py | Ph | NMR: 3.82(3H, s), 6.83–6.86(2H, m), 7.07(1H, t), 7.13(1H, d), 7.42–7.43(3H, m), 7.63–7.73(5H, m), 8.03(1H, brs), 8.35(1H, d), 8.82(1H, d). |
| 14 | 2-MeO—Ph | 4-Py | Ph | NMR: 3.82(3H, s), 6.79(1H, dd), 6.86(1H, dt), 7.08(1H, dt), 7.13(1H, dd), 7.42–7.44(3H, m), 7.54(1H, d), 7.76–7.79(2H, m), 7.85(1H, d), 8.17(2H, dd), 8.76(2H, dd). |
| 15 | 2-MeO—Ph | 3-Py | Ph | NMR: 3.83(3H, s), 6.80(1H, d), 6.87(1H, t), 7.09(1H, t), 7.14(1H, d), 7.43–7.44(3H, m), 7.56–7.59(2H, m), 7.76(2H, m), 7.85(1H, d), 8.58(1H, d), 8.74(1H, m), 9.39(1H, s). |
| 16 | 2-MeO—Ph | 6-Cl-3-Py | Ph | NMR: 3.82(3H, s), 6.81(1H, dd), 6.86(1H, dt), 7.09(1H, dt), 7.14(1H, dd), 7.40–7.47(3H, m), 7.57(1H, d), 7.68(1H, d), 7.75–7.91(2H, m), 7.84(1H, d), 8.57(1H, dd), 9.16(1H, d). |
| 17 | 2-MeO—Ph | 6-CF₃-3-Py | Ph | NMR: 3.99(3H, s), 6.95(1H, dt), 7.05(1H, dd), 7.14(1H, dd), 7.18–7.20(1H, m), 7.24(1H, d), 7.37–7.44(3H, m), 7.47–7.49(2H, m), 7.91(1H, d), 8.04(1H, dd), 8.51(1H, d), 8.95(1H, brs), 9.06(1H, brs). |
| 18 | 2-MeO—Ph | 2-The | Ph | NMR: 3.82(3H, s), 6.77(1H, dd), 6.84(1H, dt), 7.07(1H, dt), 7.13(1H, dd), 7.18(1H, t), 7.43–7.45(3H, m), 7.55(1H, d), 7.75–7.78(5H, m), 11.94(1H, brs). |
| 19 | 2-MeO—Ph | 3-The | Ph | NMR: 3.82(3H, s), 6.75(1H, dd), 6.86(1H, dt), 7.07(1H, dt), 7.13(1H, dd), 7.40–7.47(3H, m), 7.55(1H, d), 7.63(1H, dd), 7.67(1H, dd), 7.77–7.80(2H, m), 7.86(1H, d), 8.32(1H, dd), 11.86(1H, brs). |
| 20 | 2-MeO—Ph | 2-Me-4-Thi | Ph | NMR: 2.78(3H, s), 3.81(3H, s), 6.76(1H, dd), 6.86(1H, dt), 7.07(1H, dt), 7.13(1H, dd), |

TABLE 3-continued

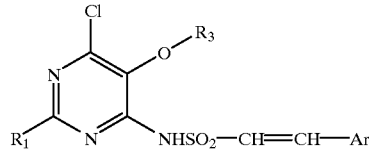

| Ref | R₃ | R₁ | Ar | |
|---|---|---|---|---|
| | | | | 7.42–7.46(3H, m), 7.74–7.82(3H, m), 7.88(1H, d), 8.33(1H, s), 11.97(1H, brs). |
| 21 | 2-MeO—Ph | 3-Fur | Ph | NMR: 3.82(3H, s), 6.74(1H, dd), 6.86(1H, dt), 6.94(1H, d).7.07(1H, dt), 7.13(1H, dd), 7.42–7.47(3H, m), 7.55(1H, d), 7.76–7.81(3H, m), 7.84(1H, d), 8.38(1H, s), 13.34(1H, brs). |

TABLE 4

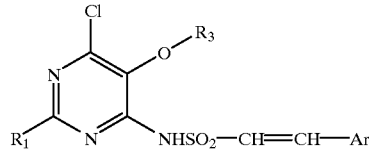

| Ref | R₄ | R₅ | Ar | |
|---|---|---|---|---|
| 22 | Me | H | Ph | NMR: 2.20(3H, s), 3.81(3H, s), 6.82(1H, d), 6.88(1H, t), 7.09(1H, t), 7.14(1H, d), 7.34–7.48(6H, m), 7.65(1H, s), 7.94(1H, brs), 8.95(2H, m). |
| 23 | Et | H | Ph | NMR: 1.06(3H, m), 2.67(2H, m), 3.81(3H, s), 6.80(1H, d), 6.88(1H, t), 7.09(1H, t), 7.14(1H, d), 7.36–7.46(5H, m), 7.67(1H, s), 8.01(1H, brs), 8.96(2H, m), 11.99(1H, brs). |
| 24 | H | H | 4-Me—Ph | NMR: 2.33(3H, s), 3.80(3H, s), 6.82(1H, d), 6.87(1H, t), 7.08(1H, t), 7.13(1H, t), 7.26(2H, d), 7.63(2H, d), 7.72(1H, t), 7.79–7.90(2H, m), 9.19(2H, d). |
| 25 | H | H | 4-tBu—Ph | NMR: 1.27(9H, t), 3.84(3H, s), 6.82(1H, dd), 6.87(1H, dt), 7.09((1H, dt), 7.14(1H, dd), 7.45(2H, d), 7.68(2H, d), 7.74(1H, t), 7.80–7.95(2H, m), 9.13(2H, d). |
| 26 | H | H | 4-Cl—Ph | NMR: 3.80(3H, s), 6.82(1H, dd), 6.87(1H, dt), 7.09(1H, dt), 7.13(1H, dd), 7.53(2H, d), 7.71(1H, t), 7.79(2H, d), 7.85–7.95(2H, m), 9.09(2H, d). |
| 27 | H | H | 2-The | N.P. |
| 28 | H | H | 4-CF₃—Ph | NMR: 3.81(3H, s), 6.81–6.90(2H, m), 7.06–7.16(2H, m), 7.72(1H, dd), 7.84(2H, d), 7.92–8.08(4H, m), 9.11(2H, d). |
| 29 | H | H | 4-MeO—Ph | NMR: 3.80(6H, s), 6.77–6.90(2H, m), 7.01(2H, d), 7.06–7.16(2H, m), 7.66–7.90(5H, m), 9.11(2H, d). |
| 30 | H | H | 2-Naph | NMR: 3.81(3H, s), 6.70–6.90(2H, m), 7.00–7.20(2H, m), 7.40–8.25(10H, m), 9.13(2H, d). |
| 31 | H | H | 1-Naph | NMR: 3.80(3H, s), 6.85(1H, d), 6.87(1H, dd), 7.09(1H, dd), 7.14(1H, d), 7.54–7.66(4H, m), 7.91(1H, d), 8.01(2H, d), 8.05(1H, d), 8.16(1H, d), 8.60(1H, d), 8.94(2H, d). |
| 32 | H | H | 2-Cl—Ph | N.P. |
| 33 | H | H | 4-MeOOC—Ph | NMR: 3.81(3H, s), 3.87(3H, s), 6.82(1H, d), 6.86(1H, dd), 7.08(1H, dd), 7.14(1H, d), 7.72(1H, dd), 7.87–8.05(6H, m), 9.10(1H, d). |
| 34 | H | H | 3-The | NMR: 3.80(3H, s), 6.82(1H, d), 6.87(1H, dd), 7.09(1H, dd), 7.12(1H, d), 7.54(1H, d), 7.62(1H, d), 7.64(1H, d), 7.71(1H, dd), 7.97(1H, d), 8.03(1H, s), 9.11(2H, d). |

TABLE 4-continued

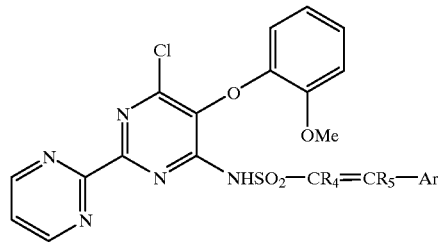

| Ref | $R_4$ | $R_5$ | Ar |  |
|---|---|---|---|---|
| 35 | H | H | 3-Cl—Ph | NMR: 3.81(3H, s), 6.82(1H, d), 6.86(1H, dd), 7.09(1H, dd), 7.13(1H, d), 7.46–7.53(2H, m), 7.71(1H, d), 7.73(1H, dd), 7.85(1H, d), 7.87(1H, s), 7.98(1H, d), 9.09(2H, d). |
| 36 | nPr | H | Ph | NMR: 0.85(3H, t), 1.57(2H, m), 2.60(2H, m), 3.81(3H, s), 6.78(1H, d), 6.87(1H, t), 7.09(1H, t), 7.14(1H, d), 7.38–7.45(5H, m), 7.65(1H, brs), 8.02(1H, m), 8.94(2H, m) 12.0(1H, brs). |
| 37 | H | Me | Ph | N.P. |
| 38 | H | H | 2-Me—Ph | NMR: 2.35(3H, s), 3.80(3H, s), 6.68–7.50(7H, m), 7.60–8.20(4H, m), 9.04(2H, m). |
| 39 | H | H | 2,4,6-triMe—Ph | NMR: 2.23(3H, s), 2.25(6H, s), 3.80(3H, s), 6.82(1H, d), 6.88(1H, dd), 6.92(2H, s), 7.10(1H, dd), 7.14(1H, d), 7.54(1H, d), 7.65(1H, dd), 7.84(1H, d), 8.96(2H, d). |

TABLE 5

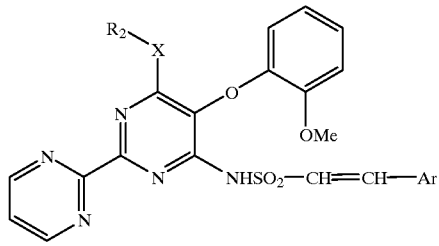

| Ex. | —X—$R_2$ | Ar | Sa |  |
|---|---|---|---|---|
| 1 | —OCH$_2$CH$_2$OH | Ph | K | ana: (C$_{25}$H$_{22}$N$_5$O$_6$SK.0.8H$_2$O) C(%) H(%) N(%) O(%) S(%) K(%) tho 52.31 4.14 12.20 18.95 5.59 6.81 fou 52.50 4.40 12.08    5.43 NMR: 3.51(2H, m), 3.84(3H, s), 4.30(2H, m), 4.87(1H, m), 6.44(1H, m), 6.74(1H, m), 6.88(1H, m), 7.02(1H, d), 7.13(1H, m), 7.33(1H, m), 7.40(2H, m), 7.60–7.62(3H, m), 8.20(1H, d), 9.02(2H, d) |
| 2 | —OMe | Ph | — | mp.: 107–109° C. NMR: 3.82(3H, s), 3.97(3H, s), 6.66(1H, d), 6.82(1H, t), 7.02(1H, d), 7.09(1H, d), 7.45(3H, m), 7.60–7.80(3H, m), 7.80(1H, d), 7.98(1H, d), 9.08(2H, d), 11.46(1H, brs) |
| 3 | —OEt | Ph | — | mp.: 173–174° C. NMR: 1.07(3H, m), 3.82(3H, s), 4.37(2H, m), 6.74(1H, d), 6.83(1H, t), 7.05–7.10(2H, m), 7.46(3H, m), 7.68–7.74(3H, m), 7.82(1H, d), 7.99(1H, d), 9.08(2H, d), 11.43(1H, brs) |
| 4 | —O-nPr | Ph | — | mp.: 161–162° C. NMR: 0.62(3H, t), 1.46(2H, m), 3.81(3H, s), 4.26(2H, m), 6.76(1H, d), 6.83(1H, t), 7.04(1H, t), 7.09(1H, d), 7.45(3H, m), 7.67(1H, m), 7.73(2H, m), 7.82(1H, d), 7.99(1H, d), 9.07(2H, d), 11.45(1H, brs) |
| 5 | —OCH$_2$-cPr | Ph | — | mp.: 134–135° C. NMR: 0.13(2H, m), 0.35(2H, m), 1.01(1H, m), 3.82(3H, s), 4.19(2H, m), 6.76(1H, d), 6.84(1H, m), |

TABLE 5-continued

| Ex. | —X—R$_2$ | Ar | Sa | |
|---|---|---|---|---|
| | | | | 7.05(1H, m), 7.10(1H, d), 7.45(3H, m), 7.67(1H, m), 7.73(2H, m), 7.81(1H, d), 7.98(1H, d), 9.06(2H, d), 11.39(1H, brs) |
| 6 | —OCH$_2$CH$_2$OCH$_3$ | Ph | — | mp.: 129–130° C. NMR: 3.08(3H, s), 3.40(2H, m), 3.82(3H, s), 4.47(2H, m), 6.77(1H, d), 6.83(1H, m), 7.05(1H, m), 7.09(1H, d), 7.45(3H, m), 7.68(1H, m), 7.73(2H, m), 7.82(1H, d), 7.99(1H, d), 9.07(2H, m), 11.41(1H, brs) |
| 7 | —OCH(CH$_3$)$_2$ | Ph | — | mp.: 145–147° C. NMR: 0.95–1.15(6H, m), 3.81(3H, s), 5.32(1H, m), 6.79(1H, m), 6.84(1H, m), 6.95–7.15(2H, m), 7.45(3H, m), 7.45–8.90(4H, m), 7.99(1H, d), 9.06(2H, d), 11.34(1H, brs) |
| 8 | —OCH$_2$CH$_2$F | Ph | — | mp.: 114–143° C. NMR: 3.82(3H, s), 4.40–4.70(4H, m), 6.79(1H, d), 6.83(1H, m), 7.05(1H, m), 7.10(1H, d), 7.45(3H, m), 7.68(1H, m), 7.74(2H, m), 7.84(1H, d), 7.97(1H, d), 9.08(2H, d), 11.47(1H, brs) |
| 9 | —OCH$_2$CHF$_2$ | Ph | — | mp.: 190–191° C. NMR: 3.81(3H, s), 4.66(2H, t), 6.15(1H, t), 6.79(1H, d), 6.83(1H, m), 7.05(1H, m), 6.84(1H, d), 7.45(3H, m), 7.70(1H, m), 7.74(2H, m), 7.86(1H, d), 7.97(1H, D), 9.09(2H, d), 11.57(1H, brs) |
| 10 | —OCH$_2$CF$_3$ | Ph | — | mp.: 204–205° C. NMR: 3.81(3H, s), 5.03(2H, q), 6.80–6.86(2H, m), 7.04–7.10(2H, m), 7.45(3H, m), 7.69(1H, m), 7.74(2H, m), 7.87(1H, d), 7.95(1H, d), 9.09(2H, d), 11.67(1H, brs) |
| 11 | —NHCH$_2$CH$_2$OH | Ph | — | ana: (C$_{25}$H$_{24}$N$_6$O$_5$S.0.3H$_2$O)     C(%)  H(%)  N(%)  O(%)  S(%) tho  57.09  4.71  15.98  16.12  6.10 fou  56.96  4.44  15.76        6.10 NMR(DMSO-d$_6$, 100° C.): 3.57(4H, m), 3.88(3H, s), 4.47(1H, m), 6.30–6.70(6H, m), 6.70–6.95(7H, m), 9.06(2H, m), 13.26(1H, brs) |
| 12 | —O(CH$_2$)$_3$OH | Ph | — | mp.: 190–191° C. NMR(CDCl$_3$): 1.86–1.92(2H, m), 3.56(2H, d, J=4.9Hz), 3.98(3H, s), 4.80(2H, t, J=5.5Hz), 5.20(1H, brs), 6.89(1H, t), 7.00(1H, d, J=7.3Hz), 7.10–7.14(2H, m), 7.36–7.40(4H, m), 7.57–7.58(2H, m), 7.62(1H, d), 8.04(1H, d), 8.81(1H, brs), 8.95(2H, d, J=4.3Hz) |
| 13 | —OCH$_2$C≡CH | Ph | — | mp: 183–185° C. NMR(CDCl$_3$): 2.45(1H, t, J=2.4Hz), 4.00(3H, s), 5.22(2H, d, J=2.4Hz), 6.91(1H, t), 7.00(1H, d, J=7.3Hz), 7.14(1H, t), 7.25–7.26(1H, m), 7.38–7.41(4H, m), 7.56–7.57(2H, m), 7.63(1H, m), 7.98(1H, d), 8.93(1H, s), 8.95(2H, d, J=4.9Hz) |
| 14 | —OCH$_2$CH$_2$OH | 3-Me—Ph | — | mp.: 167–169° C. NMR: 2.34(3H, s), 3.50(2H, m), 3.83(3H, s), 4.37(2H, m), 4.69(1H, m), 6.79–6.83(2H, m), 7.09–7.10(2H, m), 7.26(1H, d), 7.33(1H, t), 7.53(2H, m), 7.69(1H, m) 7.77(1H, d), 7.95(1H, d), 9.08(2H, d), 11.43(1H, brs) |
| 15 (a) | —OMe | Ph | K | mp.: 201–203° C. NMR: 3.80(3H, s), 3.85(3H, s), 6.40(1H, dd, J=1.6, 8.0Hz), 6.73(1H, dt, J=1.6, 8.0Hz), 6.87(1H, dt, J=1.6, 8.0Hz), 7.01(1H, dd, J=1.6, 8.0Hz), 7.12(1H, d, J=16Hz), 7.31(1H, d), 7.38–7.42(2H, m), 7.57–7.63(3H, m), 8.21(1H, d, J=16Hz), 9.03(2H, d, J=4.8Hz). |

TABLE 5-continued

| Ex. | —X—R₂ | Ar | Sa | | |
|---|---|---|---|---|---|
| 15 (b) | —OMe | Ph | Na | mp: | 192–195° C. |
| | | | | NMR: | 3.82(3H, s), 3.85(3H, s), 6.41(1H, dd, J=1.6, 7.6Hz), 6.74(1H, t, J=7.6Hz), 6.88(1H, dt, J=1.6, 7.6Hz), 7.02(1H, d, J=7.6Hz), 7.13(1H, d, J=16Hz), 7.31(1H, m), 7.35–7.41(2H, m), 7.51–7.56(2H, m), 7.63(1H, t, J=4.8Hz), 7.87(1H, d, J=16Hz), 9.01(2H, d, J=4.8Hz) |

TABLE 6

| Ex. | -X-R₂ | Ar | Sa | | |
|---|---|---|---|---|---|
| 16 | —OMe | Ph | — | mp.: | 227–230° C. |
| | | | | NMR: | 0.97(3H, t), 1.71(2H, m), 2.80(2H, m), 3.82 (3H, s), 3.88(3H, s), 6.64(1H, m), 7.45(3H, m), 7.60–7.80(5H, m), 7.84(1H, s), 7.95(1H, m), 9.07(2H, d), 11.70(1H, brs) |

TABLE 7

| Ex. | -X-R₂ | R₁ | Sa | | |
|---|---|---|---|---|---|
| 17 | —OMe | CF₃ | — | NMR: | 3.80(3H, s), 3.83(3H, s), 6.73(1H, m), 6.81 (1H, m), 7.03(1H, m), 7.08(1H, m), 7.46–7.47(3H, m), 7.66–7.70(3H, m), 11.79(1H, m). |
| | | | | m/z: | 482(FAB, M⁺ + 1) |
| 18 | —OMe | cPr | K | NMR: | 0.84(2H, m), 0.92(2H, m), 1.88(1H,m), 3.70 (3H, s), 3.82(3H, s), 6.34(1H, m), 6.73(1H, m), 6.85(1H, m), 6.98(1H, m), 7.38–7.41 (4H, m), 7.52(2H, m). |
| | | | | m/z: | 530(FAB, M⁺ + K) |

TABLE 7-continued

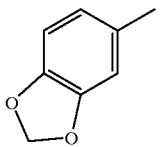

| Ex. | -X-R$_2$ | R$_1$ | Sa | | |
|---|---|---|---|---|---|
| 19 | —OMe | Ph | — | mp.: | 147–148° C. |
| | | | | NMR: | 3.85(3H, s), 3.92(3H, s), 6.66(1H, d), 6.82 (1H, t), 7.04(1H, t), 7.10(1H, d), 7.43– 7.51(6H, m), 7.56(1H, d), 7.74–7.76(2H, d) 7.81(1H, d), 8.29(2H, d), 11.23(1H, brs) |
| 20 | —OMe | 4-CF$_3$-Ph | — | mp.: | 143–144° C. |
| | | | | NMR: | 3.85(3H, s), 3.94(3H, s), 6.69(1H, d), 6.83 (1H, t), 7.03(1H, t), 7.10(1H, d), 7.42– 7.43(3H, m), 7.56(1H, d), 7.69–7.84(3H, m), 8.48(2H, d), 11.36(1H, s). |
| 21 | —OMe | 3-NO$_2$-Ph | — | mp.: | 235–236° C. |
| | | | | NMR: | 3.84(3H, s), 3.96(3H, s), 6.71(1H, d), 6.83 (1H, m), 7.03(1H, m), 7.10(1H, m), 7.38– 7.44(3H, m), 7.56(1H, d), 7.68–7.74(2H, m), 7.77–7.83(2H, m), 8.36(1H, m), 8.70(1H, m), 9.05(1H, t), 11.38(1H, brs). |
| 22 | —OMe | 3,5-diMeO-Ph | — | mp.: | 164–165° C. |
| | | | | NMR: | 3.79(6H, s), 3.84(3H, s), 3.92(3H, s), 6.64– 6.70(2H, m), 6.82(1H, t), 7.73((1H, t), 7.09(1H, d), 7.40–7.48(5H, m), 7.56(1H, d), 7.64–7.70(2H, m), 7.72(1H, d), 11.23(1H, brs). |
| 23 | —OMe | 3-MeO-Ph | — | mp.: | 161–162° C. |
| | | | | NMR: | 3.80(3H, s), 3.85(3H, s), 3.92(3H, s), 6.66 (1H, d), 6.82(1H, t), 7.03(1H, t), 7.05– 7.13(2H, m), 7.38(1H, t), 7.35–7.45(2H, m), 7.56(1H, d), 7.70–7.74(2H, m), 7.77(1H, d), 7.84(1H, d), 7.88(1H, d), 11.26(1H, s). |
| 24 | —OMe | benzo[1,3]dioxol-5-yl (methyl-substituted) | — | mp.: | 158–159° C. |
| | | | | NMR: | 3.85(3H, s), 3.90(3H, s), 6.11(2H, s), 6.64(1H, d), 6.83(1H, t), 6.97–7.04(2H, m), 7.09(1H, d), 7.42–7.47(3H, m), 7.54(1H, d), 7.71–7.79(4H, m), 7.90(1H, d), 11.20(1H, s). |
| 25 | —OMe | 3,4,5-tri MeO-Ph | — | mp.: | 153–154° C. |
| | | | | NMR: | 3.73(3H, s), 3.78(6H, s), 3.84(3H, s), 3.94 (3H, s), 6.64(1H, dd), 6.82(1H, dt), 7.03 (1H, dt), 7.09(1H, dd), 7.38–7.46(3H, m), 7.56–7.72(6H, m), 11.26(1H, s). |
| 26 | —OMe | 2-Py | — | mp.: | 88–90° C. |
| | | | | m/z: | 530(FAB, M$^+$ + 1) |
| 27 | —OMe | 4-Py | — | mp.: | 212–214° C. |
| | | | | NMR: | 3.84(3H, s), 3.93(3H, s), 6.69(1H, dd), 6.82 (1H, dt), 7.03(1H, dt), 7.10(1H, dd), 7.43– 7.45(3H, m), 7.56(1H, d), 7.77–7.79(2H, m), 7.84(1H, d), 8.16(2H, dd), 8.71(2H, dd), 11.43(1H, brs). |
| 28 | —OMe | 3-Py | — | mp.: | 168–169° C. |
| | | | | NMR: | 3.84(3H, s), 3.94(3H, s), 6.68(1H, d), 6.82 (1H, t), 7.03(1H, t), 7.10(1H, d), 7.43– 7.44(3H, m), 7.52(1H, m), 7.57(1H, d), 7.74– 7.75(2H, m), 7.80(1H, d), 8.56(1H, d), 8.70 (1H, d), 9.44(1H, s), 11.38(1H, s). |
| 29 | —OMe | 6-MeO-3-Py | — | mp.: | 156–157° C. |
| | | | | NMR: | 3.85(3H, s), 3.91(3H, s), 6.65(1H, dd), 6.82 (1H, dt), 6.89(1H, d), 7.02(1H, dt), 7.09 (1H, dd), 7.41–7.47(3H, m), 7.55(1H, d), 7.72–7.79(3H, m), 8.47(1H, dd), 9.07(2H, d), 11.27(1H, s). |
| 30 | —OMe | 6-CF$_3$-3-Py | — | mp.: | 169–170.5° C. |
| | | | | NMR: | 3.84(3H, s), 3.93(3H, s), 6.70(1H, d), 6.82 (1H, t), 7.03(1H, t), 7.10(1H, dd), 7.42– |

TABLE 7-continued

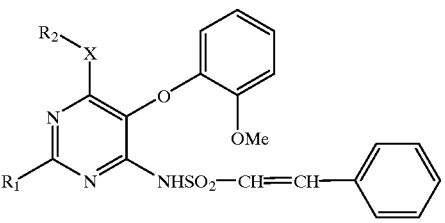

| Ex. | -X-R$_2$ | R$_1$ | Sa | | |
|-----|----------|-------|-----|---|---|
| | | | | | 7.44(3H, m), 7.72–7.76(3H, m), 7.85(1H, d), 8.38(1H, d), 8.55(1H, d), 9.18(1H, s), 11.49(1H, brs). |
| 31 | —OMe | 2-The | — | mp.: | 180–181° C. |
| | | | | NMR: | 3.84(3H, s), 3.87(3H, s), 6.65(1H, dd), 6.81 (1H, dt), 7.02(1H, t), 7.09(1H, dd), 7.17 (1H, dd), 7.42–7.46(3H, m), 7.56(1H, d), 7.72–7.80(3H, m), 7.86(1H, dd), 11.27(1H, s). |
| 32 | —OMe | 3-The | — | mp.: | 162–163° C. |
| | | | | NMR: | 3.84(3H, s), 3.89(3H, s), 6.63(1H, dd), 6.81 (1H, dt), 7.02(1H, dt), 7.09(1H, dd), 7.40– 7.46(3H, m), 7.54(1H, d), 7.62(1H, dd), 7.70–7.80(4H, m), 8.27(1H, dd), 11.17(1H, s). |
| 33 | —OMe | 2-Me-4-Thi | — | mp.: | 90–92° C. |
| | | | | NMR: | 2.80(3H, s), 3.83(3H, s), 3.89(3H, s), 6.62 (1H, d), 6.81(1H, t), 7.01(1H, t), 7.09 (1H, d), 7.42–7.48(3H, m), 7.74–7.84(3H, m), 7.91(1H, d), 8.30(1H, s), 11.31(1H, s). |
| 34 | —OMe | 3-Fur | — | mp.: | 170–171° C. |
| | | | | NMR: | 3.84(3H, s), 3.86(3H, s), 6.63(1H, dd), 6.81 (1H, dt), 6.95(1H, d), 7.01(1H, dt), 7.08 (1H, dd), 7.42–7.46(3H, m), 7.54(1H, d), 7.72–7.78(4H, m), 8.33(1H, d), 11.14(1H, s). |
| 35 | —OCH$_2$C≡CH | 6-CF$_3$-3-Py | — | mp.: | 172–174° C. |
| | | | | NMR: | 3.49(1H, s), 3.84(3H, s), 5.10(2H, s), 6.72 (1H, d), 6.83(1H, t), 7.05(1H, t), 7.11 (1H, dd), 7.42–7.44(3H, m), 7.75(3H, m), 7.87 (1H, d), 8.40(1H, d), 8.57(1H, d), 9.20 (1H, s), 11.57(1H, brs). |
| 36 | —OCH$_2$CH$_2$OH | 6-CF$_3$-3-Py | — | mp.: | 175–176.5° C. |
| | | | | NMR: | 3.52(2H, t), 3.83(3H, s), 4.41(2H, t), 6.80– 6.86(2H, m), 7.05(1H, dt), 7.10(1H, d), 7.42–7.43(3H, m), 7.72–7.76(3H, m), 7.86 (1H, d), 8.37(1H, d), 8.53(1H, d), 8.17(1H, s), 11.36(1H, s). |

TABLE 8

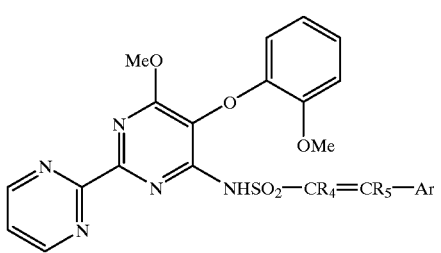

| Ex. | R$_4$ | R$_5$ | Ar | Sa | | |
|-----|-------|-------|-----|-----|---|---|
| 37 | Me | H | Ph | — | mp.: | 148–149° C. |
| | | | | | NMR: | 2.21(3H, s), 3.83(3H, s), 4.01(3H, s), 6.65 (1H, d), 6.83(1H, t), 7.03(1H, t), 7.09(1H d), 7.22– 7.41(5H, m), 7.61(1H, m), 7.87(1H, s), 9.18 (2H, d), 11.29(1H, brs). |

TABLE 8-continued

[Chemical structure: pyrimidine with MeO, OPh(OMe), linked to pyrimidine and NHSO₂—CR₄=CR₅—Ar]

| Ex. | R₄ | R₅ | Ar | Sa | | |
|---|---|---|---|---|---|---|
| 38 | Et | H | Ph | K | NMR: | 1.00(3H, t), 2.39(2H, q), 3.78(3H, s), 3.83 (3H, s), 6.41(1H, d), 6.73(1H, t), 6.87(1H, t), 7.00(1H, d), 7.17(2H, d), 7.24(1H, m), 7.30–7.35(3H, m), 7.54(1H, t), 8.89(2H, d). |
| | | | | | m/z: | 596(FAB, M⁺ + K) |
| 39 | H | H | 4-Me-Ph | — | mp.: | 165–166° C. |
| | | | | | NMR: | 2.33(3H, s), 3.83(3H, s), 4.01(3H, s), 6.66(1H, d), 6.82(1H, t), 7.03(1H, t), 7.09(1H, t), 7.27 (2H, d), 7.62(2H, d), 7.69(1H, m), 7.72(1H, d), 7.92(1H, d), 9.09(2H, d), 11.42(1H, brs). |
| 40 | H | H | 4-tBu–Ph | K | NMR: | 1.28(9H, s), 3.80(3H, s), 3.98(3H, s), 6.39 (1H, d), 6.73(1H, t), 6.87(1H, t), 7.01(1H, d), 7.12(1H, d), 7.41(2H, d), 7.50(2H, d), 7.62(1H, t), 8.13(1H, d), 9.05(2H, d). |
| | | | | | m/z: | 624(FAB, M⁺ + K) |
| 41 | H | H | 4-Cl-Ph | — | NMR: | 3.80(3H, s), 4.01(3H, s), 6.67(1H, d), 6.82 (1H, t), 7.03(1H, t), 7.09(1H, d), 7.38(2H, d), 7.67(1H, m), 7.79–7.95(3H, m), 8.02(1H, d), 9.09(2H, d), 11.52(1H, brs). |
| | | | | | m/z: | 526(FAB, M⁺ + 1) |
| 42 | H | H | 2-The | — | NMR: | 3.83(3H, s), 3.90(3H, s), 6.66(1H, d), 6.82 (1H, t), 7.03(1H, t), 7.09(1H, d), 7.16(1H, t), 7.58(1H, m), 7.67–7.71(2H, m), 7.76(1H, d), 8.03(1H, d), 9.10(2H, d), 11.48(1H, brs). |
| | | | | | m/z: | 498(FAB, M⁺ + 1) |
| 43 | H | H | 4-CF₃-Ph | K | NMR: | 3.80(3H, s), 3.85(3H, s), 6.40(1H, d), 6.74 (1H, dd), 6.88(1H, dd), 7.02(1H, d), 7.20(1H, d), 7.62(1H, dd), 7.79(2H, d), 7.85(2H, d), 8.43 (1H, d), 9.06(2H, d). |
| | | | | | m/z: | 635(FAB, M⁺ + K − 1) |
| 44 | H | H | 4-MeO–Ph | — | NMR: | 3.80(3H, s), 3.83(3H, s), 3.89(3H, s), 6.60–8.00(11H, m), 9.10(2H, d). |
| | | | | | m/z: | 520(FAB, M⁺ + 1) |
| 45 | H | H | 2-Naph | — | NMR: | 3.83(3H, s), 3.90(3H, s), 6.60–7.20(4H, m), 7.40–8.30(10H, m), 9.13(2H, d). |
| | | | | | m/z: | 540(FAB, M⁺ + 1) |
| 46 | H | H | 1-Naph | — | NMR: | 3.83(3H, s), 3.89(3H, s), 6.69(1H, d), 6.82 (1H, dd), 7.03(1H, dd), 7.10(1H, d), 7.53–7.64 (4H, m), 7.97–8.08(4H, m), 8.14(1H, d), 8.53 (1H, d), 8.93(2H, d), 11.51(1H, s). |
| | | | | | m/z: | 540(FAB, M⁺ − 1) |
| 47 | H | H | 2-Cl-Ph | — | mp.: | 97–98° C. |
| | | | | | NMR: | 3.83(3H, s), 3.91(3H, s), 6.68(1H, d), 6.82 (1H, t), 7.03(1H, t), 7.09(1H, d), 7.46–7.50 (2H, m), 7.57(1H, brd), 7.66(1H, brs), 7.95(2H, brs), 8.14(1H, brd), 9.02(2H, brs). |
| 48 | H | H | 4-HOOC-Ph | — | mp.: | >250° C. |
| | | | | | NMR: | 3.83(3H, s), 3.90(3H, s), 6.68(1H, d), 6.82 (1H, dd), 7.03(1H, dd), 7.10(1H, d), 7.69(1H, d), 7.79–7.93(3H, m), 8.05(2H, d), 8.12(1H, d), 9.10(2H, d), 11.59(1H, s), 13.15(1H, s). |
| 49 | H | H | 4-MeOOC-Ph | — | mp.: | 178–179° C. |
| | | | | | NMR: | 3.83(3H, s), 3.87(3H, s), 3.89(3H, s), 6.67 (1H, d), 6.81(1H, dd), 7.02(1H, dd), 7.09(1H, d), 7.69(1H, dd), 7.80–7.96(3H, m), 8.03(2H, d), 8.13(1H, d), 9.09(2H, d), 11.60(1H, s). |
| 50 | H | H | 3-The | — | NMR: | 3.83(3H, s), 3.89(3H, s), 6.66(1H, d), 6.82 (1H, dd), 7.03(1H, dd), 7.10(1H, d), 7.53(1H, d), 7.62–7.76(3H, m), 7.88(1H, d), 8.01(1H, s), 9.09(2H, d), 11.42(1H, s). |
| | | | | | m/z: | 498(FAB, M⁺ + 1), 520(FAB, M⁺ + Na) |
| 51 | H | H | 3-Cl-Ph | — | NMR: | 3.83(3H, s), 3.90(3H, s), 6.68(1H, d), 6.82 (1H, dd), 7.03(1H, dd), 7.09(1H, d), 7.46–7.52 |

TABLE 8-continued

[Structure: pyrimidine with MeO, O-phenyl-OMe, pyrimidinyl, and NHSO₂—CR₄=CR₅—Ar substituents]

| Ex. | R₄ | R₅ | Ar | Sa | | |
|-----|----|----|----|----|---|---|
| | | | | | | (2H, m), 7.66–7.75(2H, m), 7.80(1H, d), 7.87 (1H, s), 8.11(1H, d), 9.08(2H, d), 11.59(1H, s). |
| | | | | | m/z: | 526(FAB, M⁺ + 1), 548(FAB, M⁺ + Na) |
| 52 | nPr | H | Ph | K | NMR: | 0.70(3H, t), 1.46(2H, m), 2.34(2H, m), 3.77 (3H, s), 3.84(3H, s), 6.39(1H, dd), 6.72(1H, dt), 6.87(1H, dt), 7.01(1H, dd), 7.14–7.17(2H, m), 7.23(1H, m), 7.30–7.34(2H, m), 7.37(1H, s), 7.53(1H, t), 8.85(2H, d). |
| | | | | | mn/z: | 610(FAB, M⁺ + K) |
| 53 | H | Me | Ph | — | NMR: | 2.23(3H, d), 3.79(3H, s), 3.85(3H, s), 6.40 (1H, dd), 6.73(1H, dt), 6.87(1H, dt), 7.01(1H, dd), 7.18(1H, d), 7.26–7.34(3H, m), 7.52–7.55 (2H, m), 7.61(1H, t), 8.98(2H, d). |
| | | | | | m/z: | 528(FAB, M⁺ + Na) |
| 54 | H | H | 2-Me-Ph | — | NMR: | 2.27(3H, s), 3.82(3H, s), 3.84(3H, s), 6.40 (1H, dd), 6.62–7.08(3H, m), 7.20–7.39(4H, m), 7.56–7.67(2H, m), 8.02(1H, brd) |
| | | | | | m/z: | 506(FAB, M⁺ + 1). |
| 55 | H | H | 2,4,6-tri Me–Ph | — | NMR: | 2.24(9H, s), 3.82(3H, s), 3.91(3H, s), 6.55– 7.20(7H, m), 7.50–7.90(2H, m), 8.96(2H, d). |
| | | | | | m/z: | 534(FAB, M⁺ + 1), 556(FAB, M⁺ + Na) |

The compounds whose chemical structural formulae are given in the following Table 9 can be easily manufactured by almost the same method mentioned in the above Examples or Manufacturing Methods or by applying some modifications thereto which are obvious to the persons skilled in the art.

Abbreviations in the table have the same meanings which were defined already. Incidentally, "Co." in the table means a compound number.

TABLE 9

[Structure: pyrimidine with R₂—X, O-phenyl-OMe, pyrimidinyl, and NHSO₂—CR₄=CR₅—Ar substituents]

| Co. | R₂-X- | R₄ | R₅ | Ar | Co. | R₂-X- | R₄ | R₅ | Ar |
|-----|-------|----|----|-----|-----|-------|----|----|------|
| 1 | MeO | H | H | 2-Fur | 16 | MeO | Me | H | 2-The |
| 2 | MeO | H | H | 3-Fur | 17 | MeO | Me | H | 3-The |
| 3 | MeO | H | H | 2-Thi | 18 | MeO | Et | H | 2-The |
| 4 | MeO | H | H | 4-Thi | 19 | MeO | Et | H | 3-The |
| 5 | MeO | H | H | 5-Thi | 20 | MeS | H | H | Ph |
| 6 | MeO | H | H | 2-Py | 21 | MeS | Me | H | Ph |
| 7 | MeO | H | H | 3-Py | 22 | MeS | Et | H | Ph |
| 8 | MeO | H | H | 4-Py | 23 | MeS | H | H | 2-The |
| 9 | MeO | H | H | 5-Pym | 24 | MeS | H | H | 3-The |

TABLE 9-continued

| Co. | R$_2$-X- | R$_4$ | R$_5$ | Ar | Co. | R$_2$-X- | R$_4$ | R$_5$ | Ar |
|---|---|---|---|---|---|---|---|---|---|
| 10 | MeO | H | H | 2-MeO-Ph | 25 | MeNH | H | H | Ph |
| 11 | MeO | H | H | 3-MeO-Ph | 26 | MeNH | Me | H | Ph |
| 12 | MeO | H | H | 2-CN-Ph | 27 | MeNH | Et | H | Ph |
| 13 | MeO | H | H | 3-CN-Ph | 28 | MeNH | H | H | 2-The |
| 14 | MeO | H | H | 3-Me-Ph | 29 | MeNH | H | H | 3-The |
| 15 | MeO | H | H | 3,4-diMeO-Ph | | | | | |

What is claimed is:

1. An arylethenesulfonamide compound represented by the following formula (I) or a pharmaceutically acceptable salt thereof:

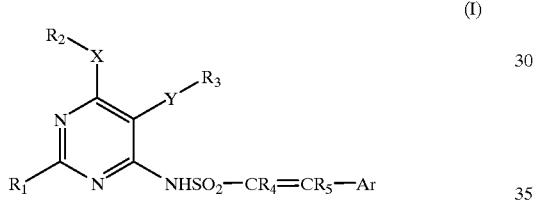

in which
Ar is a thienyl group or an aryl group which is unsubstituted or substituted with one to five identical or different substituents selected from the group consisting of lower alkyl group, lower alkoxy group, lower alkoxycarbonyl group, carboxyl group, halogen atom, nitro group, cyano group, amino group, mono-lower alkylamino group, di-lower alkylamino group, hydroxyl group and C$_{1-3}$ alkylenedioxy group, wherein said lower alkyl group is unsubstituted or substituted with one to four identical or different substituents selected from the group consisting of halogen atom, lower alkoxy group, carboxyl group, amino group, mono-lower alkylamino group, and di-lower alkylamino group;

X is oxygen atom, sulfur atom or a group represented by —NH—;

Y is oxygen atom or sulfur atom;

R$_1$ is hydrogen atom, lower alkyl group which is unsubstituted or substituted with one or more identical or different halogen atoms, cycloalkyl group, aryl group which is unsubstituted or substituted with one to five identical or different substituents selected from the group consisting of lower alkyl group, lower alkoxy group, lower alkoxycarbonyl group, carboxyl group, halogen atom, nitro group, cyano group, amino group, mono-lower alkylamino group, di-lower alkylamino group, hydroxyl group and C$_{1-3}$ alkylenedioxy group, wherein said lower alkyl group is unsubstituted or substituted with one to four identical or different substituents selected from the group consisting of halogen atom, lower alkoxy group, carboxyl group, amino group, mono-lower alkylamino group, and di-lower alkylamino group, or five- to six-membered heteroaryl group selected from the group consisting of pyrimidinyl, pyridinyl, thienyl, thiazolyl, 1,3-benzodioxanyl and furyl, wherein said heteroaryl group is unsubstituted or substituted with one to four identical or different substituents selected from the group consisting of lower alkyl group, lower alkoxy group, lower alkoxycarbonyl group, carboxyl group, halogen atom, nitro group, cyano group, amino group, mono-lower alkylamino group, and di-lower alkylamino group, wherein said lower alkyl group is unsubstituted or substituted with one to four identical or different substituents selected from the group consisting of halogen atom, lower alkoxy group, carboxyl group, amino group, mono-lower alkylamino group, and di-lower alkylamino group;

R$_2$ is lower alkyl group, lower alkenyl group or lower alkynyl group, and R$_2$ is unsubstituted or substituted with one to three identical or different substituents selected from the group consisting of hydroxyl group, lower alkoxy group, cycloalkyl group, halogen atom, carboxyl group and lower alkoxycarbonyl group;

R$_3$ is phenyl group which is unsubstituted or substituted with one to four identical or different substituents selected from the group consisting of lower alkyl group which is unsubstituted or substituted with one or more identical or different halogen atoms, lower alkoxy group, halogen atom, lower alkylthio group, lower alkylsulfinyl group, lower alkanesulfonyl group, carboxyl group, lower alkoxycarbonyl group and carbamoyl group; and R$_4$ and R$_5$ are the same or different and each is hydrogen atom or lower alkyl.

2. The arylethenesulfonamide compound or a pharmaceutically acceptable salt thereof according to claim 1 in which:

Ar is thienyl group or aryl group which is unsubstituted or substituted with one to five identical or different substituents selected from the group consisting of lower alkyl group which is unsubstituted or substituted with one or more identical or different halogen atoms, lower alkoxy group, lower alkoxycarbonyl group, carboxyl group, halogen atom, nitro group and cyano group;

X is oxygen atom or a group represented by a formula —NH—;

Y is oxygen atom;

$R_1$ is lower alkyl group which is unsubstituted or substituted with one or more identical or different halogen atoms, cycloalkyl group, aryl group which is unsubstituted or substituted with one to five identical or different substituents selected from the group consisting of lower alkyl group which is unsubstituted or substituted with one or more identical or different halogen atoms, lower alkoxy group, lower alkoxycarbonyl group, carboxyl group, halogen atom, nitro group, cyano group and $C_{1-3}$ alkylenedioxy group, or five- to six-membered heteroaryl group selected from the group consisting of pyrimidinyl, pyridinyl, thienyl, thiazolyl, 1,3-benzodioxanyl and furyl, wherein said heteroaryl group is unsubstituted or substituted with one to four identical or different substituents selected from the group consisting of lower alkyl group which is unsubstituted or substituted by one or more identical or different halogen atoms, lower alkoxy group, lower alkoxycarbonyl group, carboxyl group, halogen atom, nitro group and cyano group; and $R_3$ is phenyl group which is unsubstituted or substituted with one to four identical or different substituents selected from the group consisting of lower alkyl group which is unsubstituted or substituted with one or more identical or different halogen atoms, lower alkoxy group, halogen atom, carboxyl group and lower alkoxycarbonyl group.

3. The arylethenesulfonamide compound or a pharmaceutically acceptable salt thereof according to claim 1 in which:

Ar is thienyl group, naphthyl group or phenyl group which is unsubstituted or substituted with one to five substituents selected from the group consisting of lower alkyl group which is unsubstituted or substituted by one or more identical or different halogen atoms, lower alkoxy group and halogen atom;

$R_1$ is lower alkyl group which is unsubstituted or substituted by one or more identical or different halogen atoms; cycloalkyl group, phenyl group is unsubstituted or substituted with one to five substituents selected from a group consisting of lower alkyl group which is unsubstituted or substituted by one or more identical or different halogen atoms, lower alkoxy group, nitro group and $C_{1-3}$ alkylenedioxy group, or five- to six-membered heteroaryl group selected from the group consisting of pyrimidinyl, pyridinyl, thienyl, thiazolyl, 1,3-benzodioxanyl and furyl, wherein said heteroaryl group is unsubstituted or substituted with one to four substituents selected from the group consisting of lower alkyl group which is unsubstituted or substituted by one or more identical or different halogen atoms, and lower alkoxy group;

$R_2$ is lower alkynyl group or lower alkyl group which is unsubstituted or substituted with one to three substituents selected from the group consisting of hydroxyl group, lower alkoxy group, cycloalkyl group and halogen atom; and $R_3$ is phenyl group which is unsubstituted or substituted with one to four substituents selected from the group consisting of lower alkyl group, lower alkoxy group and lower alkoxycarbonyl group.

4. The arylethenesulfonamide compound or a pharmaceutically acceptable salt thereof according to claim 1 in which Ar is phenyl group which is unsubstituted or substituted by one or more identical or different lower alkyl groups, or thienyl group;

X is oxygen atom;

$R_1$ is phenyl group which is unsubstituted or substituted with lower alkoxy group or five- to six-membered heteroaryl group selected from the group consisting of pyrimidinyl, pyridinyl, thienyl, thiazolyl, 1,3-benzodioxanyl and furyl, wherein said heteroaryl group is unsubstituted or substituted with one or more identical or different lower alkyl groups;

$R_2$ is lower alkynyl group or lower alkyl group which is unsubstituted or substituted with one to three identical or different substituents selected from the group consisting of hydroxyl group and halogen atom; and $R_3$ is phenyl group which is substituted with one or more identical or different lower alkoxy groups.

5. The arylethenesulfonamide compound or a pharmaceutically acceptable salt thereof according to claim 1 in which Ar is phenyl group or thienyl group;

$R_1$ is pyrimidinyl group;

$R_2$ is lower alkyl group which is unsubstituted or substituted with one or more identical or different halogen atoms;

$R_3$ is phenyl group which is substituted with one or more identical or different lower alkoxy groups;

$R_4$ is hydrogen atom or lower alkyl group; and $R_5$ is hydrogen atom.

6. The arylethenesulfonamide compound according to claim 1 which is chosen from the following compounds as well as salts thereof:

N-[6-(2-hydroxyethoxy)-5-(2-methoxyphenoxy)-2-(2-pyrimidinyl)-4-pyrimidinyl]-2-phenylethenesulfonamide, N-[6-methoxy-5-(2-methoxyphenoxy)-2-(2-pyrimidinyl)-4-pyrimidinyl]-2-phenylethenesulfonamide, N-[6-(2-fluoroethoxy)-5-(2-methoxyphenoxy)-2-(2-pyrimidinyl)-4-pyrimidinyl]-2-phenylethenesulfonamide, N-[6-(2-propynyloxy)-5-(2-methoxyphenoxy)-2-(2-pyrimidinyl)-4-pyrimidinyl]-2-phenylethenesulfonamide, N-[6-methoxy-5-(2-methoxyphenoxy)-2-(2-pyrimidinyl)-4-pyrimidinyl]-1-methyl-2-phenylethenesulfonamide, N-[6-methoxy-5-(2-methoxyphenoxy)-2-(2-pyrimidinyl)-4-pyrimidinyl]-1-ethyl-2-phenylethenesulfonamide, and N-[6-methoxy-5-(2-methoxyphenoxy)-2-(2-pyrimidinyl)-4-pyrimidinyl]-2-(2-thienyl)ethenesulfonamide.

7. A pharmaceutical composition comprising:

an arylethenesulfonamide compound represented by the following formula (I) or a pharmaceutically acceptable salt thereof:

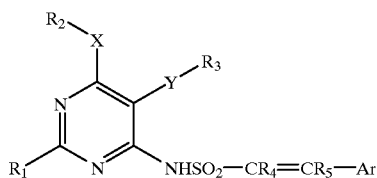

in which

Ar is a thienyl group or an aryl group which is unsubstituted or substituted with one to five identical or different substituents selected from the group consisting of lower alkyl group, lower alkoxy group, lower alkoxycarbonyl group, carboxyl group, halogen atom, nitro group, cyano group, amino group, mono-lower alkylamino group, di-lower alkylamino group, hydroxyl group and $C_{1-3}$ alkylenedioxy group, wherein said lower alkyl group is unsubstituted or substituted with one to four identical or different substituents selected from the group consisting of halogen atom, lower alkoxy group, carboxyl group, amino group, mono-lower alkylamino group, and di-lower alkylamino group;

X is oxygen atom, sulfur atom or a group represented by —NH—;

Y is oxygen atom or sulfur atom;

$R_1$ is hydrogen atom, lower alkyl group which is unsubstituted or substituted with one or more identical or different halogen atoms, cycloalkyl group, aryl group which is unsubstituted or substituted with one to five identical or different substituents selected from the group consisting of lower alkyl group, lower alkoxy group, lower alkoxycarbonyl group, carboxyl group, halogen atom, nitro group, cyano group, amino group, mono-lower alkylamino group, di-lower alkylamino group, hydroxyl group and $C_{1-3}$ alkylenedioxy group, wherein said lower alkyl group is unsubstituted or substituted with one to four identical or different substituents selected from the group consisting of halogen atom, lower alkoxy group, carboxyl group, amino group, mono-lower alkylamino group, and di-lower alkylamino group, or five- to six-membered heteroaryl group selected from the group consisting of pyrimidinyl, pyridinyl, thienyl, thiazolyl, 1,3-benzodioxanyl and furyl, wherein said heteroaryl group is unsubstituted or substituted with one to four identical or different substituents selected from the group consisting of lower alkyl group, lower alkoxy group, lower alkoxycarbonyl group, carboxyl group, halogen atom, nitro group, cyano group, amino group, mono-lower alkylamino group, and di-lower alkylamino group, wherein said lower alkyl group is unsubstituted or substituted with one to four identical or different substituents selected from the group consisting of halogen atom, lower alkoxy group, carboxyl group, amino group, mono-lower alkylamino group, and di-lower alkylamino group;

$R_2$ is lower alkyl group, lower alkenyl group or lower alkynyl group where each of which is unsubstituted or substituted with one to three identical or different substituents selected from the group consisting of hydroxyl group, lower alkoxy group, cycloalkyl group, halogen atom, carboxyl group and lower alkoxycarbonyl group;

$R_3$ is phenyl group which is unsubstituted or substituted with one to four identical or different substituents selected from the group consisting of lower alkyl group which is unsubstituted or substituted with one or more identical or different halogen atoms, lower alkoxy group, halogen atom, lower alkylthio group, lower alkylsulfinyl group, lower alkanesulfonyl group, carboxyl group, lower alkoxycarbonyl group and carbamoyl group; and $R_4$ and $R_5$ are the same or different and each is hydrogen atom or lower alkyl; and a pharmaceutically acceptable carrier.

8. A pharmaceutical composition according to claim 7 wherein said compound is an endothelin receptor antagonist.

* * * * *